(12) United States Patent
Boger

(10) Patent No.: US 7,662,971 B2
(45) Date of Patent: Feb. 16, 2010

(54) INHIBITORS OF FATTY ACID AMIDE HYDROLASE

(75) Inventor: Dale L. Boger, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 430 days.

(21) Appl. No.: 10/528,552

(22) PCT Filed: Oct. 8, 2003

(86) PCT No.: PCT/US03/31975
§ 371 (c)(1),
(2), (4) Date: Aug. 23, 2005

(87) PCT Pub. No.: WO2004/033652
PCT Pub. Date: Apr. 22, 2004

(65) Prior Publication Data
US 2006/0111359 A1    May 25, 2006

Related U.S. Application Data

(60) Provisional application No. 60/417,247, filed on Oct. 8, 2002.

(51) Int. Cl.
C07D 263/30    (2006.01)
(52) U.S. Cl. .................................. 548/235
(58) Field of Classification Search ............. 548/236, 548/235
See application file for complete search history.

(56) References Cited

U.S. PATENT DOCUMENTS

| 6,462,054 | B1 | 10/2002 | Boger | |
|---|---|---|---|---|
| 6,576,630 | B1 * | 6/2003 | Link et al. | 514/233.8 |
| 6,891,043 | B2 | 5/2005 | Boger | |
| 2002/0103192 | A1 | 8/2002 | Curtin et al. | |
| 2006/0111359 | A1 | 5/2006 | Boger | |

FOREIGN PATENT DOCUMENTS

WO    WO-2004/033652 A2    4/2004

OTHER PUBLICATIONS

Boger et al. Proceedings of the National Academy of Sciences 97 (10), 2000.*
Dondoni et. al. Journal of Organic Chemistry (1987), 52(15), 3413-20.*
Edwards, et al., "Design, Synthesis, and Kinetic Evaluation of a Unique Class of Elastase Inhibitors, the Peptidyl a-Ketobenzoxazoles, and the X-ray Crystal Structure of the Covalent Complex between Porcine Pancreatic Elastase and Ac-Ala-Pro-Val-2-Benzoxazole", *J. Am. Chem. Soc.* 114: 1854-1863 (1992).
Lerner, et al., "Cerebrodiene: A Brain Lipid isolated from sleep-deprived cats", *Proc. Natl. Acad. Sci. USA* 91: 9505-9508 (1994).
Koutek, et al., "Inhibitors of Arachidonoyl Ethanolamide Hydrolysis", *J. Biol. Chem.* 269: 22937-22940 (1994).
Cravatt, et al., "Chemical Characterization of a Family of Brain Lipids That Induce Sleep", *Science* 268: 1506-1509 (1995).
Ueda, et al., "Partial Purification and Characterization of the Porcine Brain Enzyme Hydrolyzing and Synthesizing Anandamide", *J. Biol. Chem.* 270: 23823-23827 (1995).
Cravatt, et al., "Structure Determination of an Endogenous Sleep-Inducing Lipid, cis-9-Octadecenamide (Oleamide): A Synthetic Approach to the Chemical Analysis of Trace Quantities of a Natural Product", *J. Am. Chem. Soc.* 118: 580-590 (1996).
Patterson, et al., "Inhibition of Oleamide Hydrolase Catalyzed Hydrolysis of the Endogenous Sleep-Inducing Lipid cis-9-Octadecenamide", *J. Am. Chem. Soc.* 118: 5938-5945 (1996).
Cravatt, et al., "Molecular Characterization of an Enzyme that Degrades Neuromodulatory Fatty-Acid Amides", *Nature* 384: 83-87 (1996).
Petrocellis, et al., "Novel Inhibitors of Brain, Neuronal, and Basophilic Anandamide Amidohydrolase", *Biochem. Biophys. Res. Commun.* 231: 82-88 (1997).
Deutsch, et al., "Fatty Acid Sulfonyl Fluorides Inhibit Anandamide Metabolism and Bind to the Cannabinoid Receptor", *Biochem. Biophys. Res. Commun.* 231: 217-221 (1997).
Kurahashi, et al., "Reversible Hydrolysis and Synthesis of Anandamide Demonstrated by Recombinant Rat Fatty-Acid Amide Hydrolase", *Biochem. Biophys. Res. Commun.* 237: 512-515 (1997).
Bisogno, et al., "Biosynthesis, Release and Degradation of the Novel Endogenous Cannabimimetic Metabolite 2-Arachidonoylglycerol in MouseNeuroblastoma Cells", *Biochem. J.* 322: 671-677 (1997).
Giang, et al., "Molecular Characterization of Human and Mouse Fatty Acid Amide Hydrolase", *Proc. Natl. Acad. Sci. USA* 94: 2238-2242 (1997).
Thomas, et al., "Fatty Acid Amide Hydrolase, the Degradative Enzyme for Anandamide and Oleamide, Has Selective Distribution in Neurons Within the Rat Central Nervous System", *J. Neuroscience Res.* 50: 1047-1052 (1997).
Di Marzo, et al., "The Novel Endogenous Cannabinoid 2-Arachidonoylglycerol is inactivated by neuronal- and basophil-like cells: connections with anandamide", *Biochem. J.* 331: 15-19 (1998).
Goparaju, et al., "Anandamide amidohydrolase reacting with 2-arachidonoylglycerol, another cannabinoid receptor ligand", *FEBS Lett.* 422: 69-73 (1998).

(Continued)

*Primary Examiner*—D. Margaret Seaman
*Assistant Examiner*—Nizal S Chandrakumar
(74) *Attorney, Agent, or Firm*—Schwegman, Lundberg & Woessner, P.A.

(57) ABSTRACT

Improved competitive inhibitors of FAAH employ an α-keto heterocyclic pharmacophore and a binding subunit having a ?-unsaturation. The α-keto heterocyclic pharmacophore and a binding subunit are attached to one another, preferably by a hydrocarbon chain. The improvement lies in the use of a heterocyclic pharmacophore selected from oxazoles, oxadiazoles, thiazoles, and thiadiazoles that have alkyl or aryl substituents at their 4 and/or 5 positions. The improved competitive inhibitors of FAAH display enhanced activity over conventional competitive inhibitors of FAAH.

14 Claims, 16 Drawing Sheets

OTHER PUBLICATIONS

Murillo-Rodriguez, et al., "Anandamide modulates sleep and memory in rats", *Brain Res.* 812: 270-274 (1998).

Patricelli, et al., "An Endogenous Sleep-Inducing Compound is a Novel Competitive Inhibitor of Fatty Acid Amide Hydrolase", *Bioorg. Med. Chem. Lett.* 8: 613-618 (1998).

Boger, et al., "Structural Requirements for 5-HT$_{2A}$ and 5-HT$_{1A}$ Serotonin Receptor Potentiation by the Biologically Active Lipid Oleamide", *Proc. Natl. Acad. Sci. USA* 95: 4102-4107 (1998).

Maccarrone, et al., "Anandamide Hydrolysis by Human Cells in Culture and Brain", *J. Biol. Chem.* 273: 32332-32339 (1998).

Boger, et al., "Trifluoromethyl Ketone Inhibitors of Fatty Acid Amide Hydrolase: A Probe of Structural and Conformational Features Contributing to Inhibition", *Bioorg. Med. Chem. Lett.* 9: 265-270 (1999).

Lang, et al., "Substrate Specificity and Stereoselectivity of Rat Brain Microsomal Anandamide Amidohydrolase", *J. Med. Chem* 42: 896-902 (1999).

Boger, et al., "Exceptionally potent inhibitors of fatty acid amide hydrolase: The enzyme responsible for degradation of endogenous oleamide and anandamide", *Proc. Natl. Acad. Sci. USA* 97: 5044-5049 (2000).

*Chemical Abstracts Online*, Registry No. 76115-66-7, © 2009 ACS on STN, 1 pg.

"International Application Serial No. PCT/US03/31975, International Search Report mailed Jul. 30, 2004", 1 pg.

\* cited by examiner

α-Keto Oxazole, Thiazole, Oxadiazole, and Thiadiazole
Inhibitors of Fatty Acid Amide Hydrolase (FAAH)
| compound | R | $K_i$, μM | compound | R | $K_i$, μM |
|---|---|---|---|---|---|
| 70 |  | 0.10 ±0.06 | 140 | 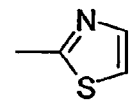 | 0.09 ±0.2 |
| 68 |  | > 100 | 141 |  | 0.17 ±0.03 |
Substituted α-Keto Oxazole Inhibitors of Fatty Acid
Amide Hydrolase (FAAH)
| compound | $R^1$ | $K_i$, μM | compound | $R^2$ | $K_i$, μM |
|---|---|---|---|---|---|
| 142 |  | 0.32 ±0.05 | 162 |  | 0.49 ±0.03 |
| 143 |  | 0.018 ±0.005 | 163 |  | 0.031 ±0.006 |
| 144 |  | 0.061 ±0.004 | 164 |  | 0.041 ±0.010 |
| 145 |  | 0.056 ±0.003 | 165 |  | 0.078 ±0.014 |
| 146 |  | | 166 | | |
| 147 |  | | 167 | | |
| 148 |  | | 168 |  | |
Figure 1

Substituted α-Keto Oxazole Inhibitors of Fatty Acid Amide Hydrolase (FAAH)

| compound | R¹ | $K_i$, μM | compound | R² | $K_i$, μM |
|---|---|---|---|---|---|
| 149 | 2-pyrimidinyl | | 169 | 2-pyrimidinyl | |
| 150 | N-Me pyrazole | 8.6 ±2.1 | 170 | N-Me pyrazole | |
| 151 | 2-thienyl | 0.89 ±0.03 | 171 | 2-thienyl | |
| 152 | 2-furyl | 0.054 ±0.004 | 172 | 2-furyl | |
| 153 | oxazol-2-yl | | 173 | oxazol-2-yl | |
| 154 | 2-thiazolyl | 0.016 ±0.002 | 174 | 2-thiazolyl | |
| 155 | N-Me imidazolyl | 0.047 ±0.006 | 175 | N-Me imidazolyl | |
| 156 | 1,3,4-oxadiazolyl | | 176 | 1,3,4-oxadiazolyl | |
| 157 | N-Me pyrrolyl | | 177 | N-Me pyrrolyl | |
| 158 | 3-thienyl | 13.2 ±4.1 | 178 | 3-thienyl | |
| 159 | 3-furyl | 0.61 ±0.09 | 179 | 3-furyl | |
| 160 | oxazol-4-yl | | 180 | oxazol-4-yl | |
| 161 | isoxazolyl | | 181 | isoxazolyl | |

Figure 2

α-Keto Oxazolopyridine Inhibitors of Fatty Acid Amide Hydrolase (FAAH)

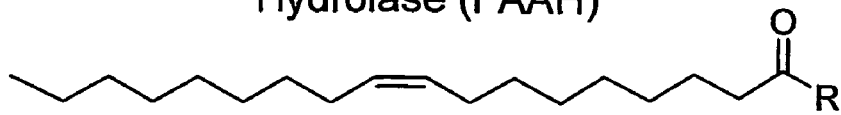

| compd | R | $K_i$, µM | compd | R | $K_i$, µM |
|---|---|---|---|---|---|
| 83 | benzoxazole | 0.37 ±0.13 | 84 | benzothiazole | > 100 |
| 89 | oxazolo[4,5-b]pyridine | 0.0023 ±0.0001 | 90 | oxazolo[4,5-c]pyridine | 0.0072 ±0.0016 |
| 91 | oxazolo[5,4-c]pyridine | 0.0037 ±0.0010 | 92 | oxazolo[5,4-b]pyridine | 0.011 ±0.004 |

- Potency increases with introduction of basic nitrogen
- Potency increases ca. 200x and N4 > N6 > N5 > N7
- Relatively insensitive to location of additional nitrogen

Figure 3

Modifications in the Fatty Acid Side Chain

| compd | R | $K_i$, µM | compd | R | $K_i$, µM |
|---|---|---|---|---|---|
| 182 | $CH_3(CH_2)_{16}$ | 0.059 ±0.014 | 195 | $Ph(CH_2)$ | 17.4 ±4.6 |
| 183 | $CH_3(CH_2)_{14}$ | 0.021 ±0.005 | 196 | $Ph(CH_2)_2$ | 0.20 ±0.6 |
| 184 | $CH_3(CH_2)_{12}$ | 0.013 ±0.005 | 197 | $Ph(CH_2)_3$ | 0.12 ±0.02 |
| 185 | $CH_3(CH_2)_{10}$ | 0.0022 ±0.0005 | 198 | $Ph(CH_2)_4$ | 0.033 ±0.002 |
| 186 | $CH_3(CH_2)_9$ | 0.0033 ±0.0006 | 199 | $Ph(CH_2)_5$ | 0.011 ±0.003 |
| 187 | $CH_3(CH_2)_8$ | 0.0090 ±0.026 | 200 | $Ph(CH_2)_6$ | 0.0047 ±0.0013 |
| 188 | $CH_3(CH_2)_7$ | 0.041 ±0.004 | 201 | $Ph(CH_2)_7$ | 0.0075 ±0.0034 |
| 189 | $CH_3(CH_2)_6$ | 0.049 ±0.005 | 202 | $Ph(CH_2)_8$ | 0.0078 ±0.0021 |
| 190 | $CH_3(CH_2)_5$ | 0.17 ±0.07 | | $Ph(CH_2)_9$ | |
| 191 | $CH_3(CH_2)_4$ | 0.94 ±0.3 | | $Ph(CH_2)_{10}$ | |
| 192 | $CH_3(CH_2)_3$ | 3.0 ±0.9 | | | |
| 193 | $CH_3(CH_2)_2$ | 11.4 ±2.2 | | | |
| 194 | $CH_3CH_2$ | 47.6 ±10.4 | | | |
| 203 | $CH_2=CH(CH_2)_7$ | 0.011 ±0.001 | 204 | $HC{\equiv}C(CH_2)_7$ | 0.023 ±0.011 |
| 205 | ~~~~~≡~~~~~ | | | | 0.010 ±0.001 |

206 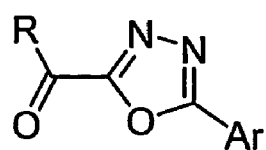 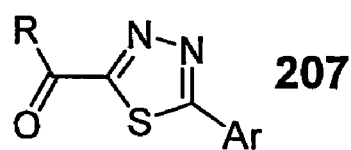 207
208 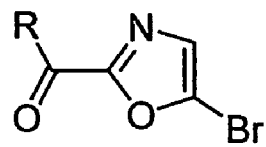 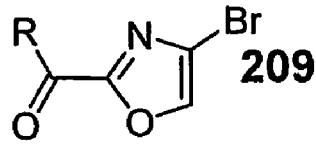 209
Pd₂(dba)₃
ArB(OH)₂
Pd₂(dba)₃
ArB(OH)₂
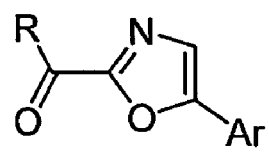 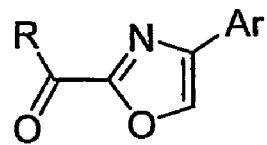
Figure 5

| compound | R | $K_i$, µM |
|---|---|---|
| 89 | 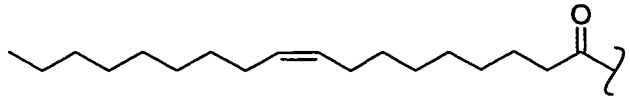 | 0.0023 ±0.0001 |
| 93 | 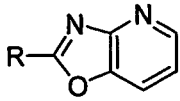 | 0.0032 ±0.0006 |
| 94 | 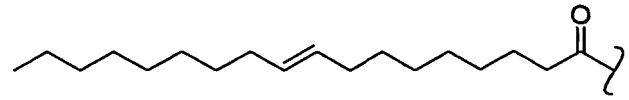 | 0.011 ±0.006 |
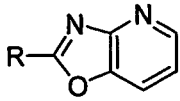
| compound | R | $K_i$, µM |
|---|---|---|
| 77 | 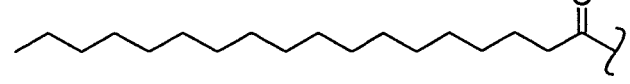 | 0.13 ±0.02 |
| 95 | 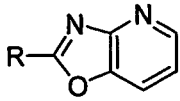 | 0.15 ±0.02 |
| 96 | 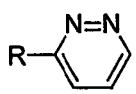 | 0.70 ±0.03 |
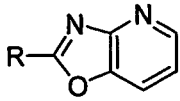
• C18 $\Delta^{9,10}$; Z(cis) > E(trans) > saturated
| compound | R | $K_i$, µM |
|---|---|---|
| 83 | 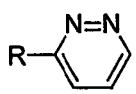 | 0.37 ±0.13 |
| 97 | 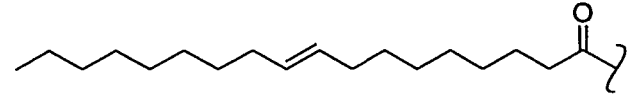 | 2.4 ±0.5 |
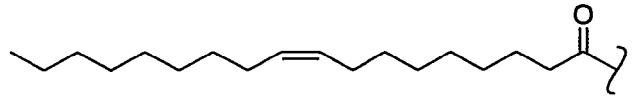
Figure 6

| compound | R | $K_i$, μM | compound | R | $K_i$, μM |
| --- | --- | --- | --- | --- | --- |
| 34 | $CH_3(CH_2)_{16}$ | 0.011 ±0.006 | 51 | $Ph(CH_2)_3$ | 0.0069 ±0.001 |
| 42 | $CH_3(CH_2)_{14}$ | 0.0019 ±0.0002 | 52 | $Ph(CH_2)_4$ | 0.00030 ±0.00009 |
| 43 | $CH_3(CH_2)_{12}$ | 0.0017 ±0.0008 | 53 | $Ph(CH_2)_5$ | 0.00020 ±0.0008 |
| 44 | $CH_3(CH_2)_{10}$ | 0.00057 ±0.00024 | 54 | $Ph(CH_2)_6$ | 0.00028 ±0.00020 |
| 45 | $CH_3(CH_2)_8$ | 0.00075 ±0.00017 | 55 | $Ph(CH_2)_7$ | 0.00039 ±0.00006 |
| 46 | $CH_3(CH_2)_6$ | 0.00069 ±0.00015 | 56 | $Ph(CH_2)_8$ | 0.00052 ±0.00018 |
| 47 | $CH_3(CH_2)_5$ | 0.0021 ±0.0003 | | | |
| 48 | $CH_3(CH_2)_4$ | 0.015 ±0.002 | | | |
| 49 | $CH_3(CH_2)_3$ | 0.050 ±0.009 | | | |
| 50 | $CH_3$ | >100 | | | |

- C18 < C16 < C14 < C12-C8 > C7 > C6 > C5 > C2

$K_I$ = 200 pM

- $Ph(CH_2)_3$ < $Ph(CH_2)_4$ < $Ph(CH_2)_5$ > $Ph(CH_2)_6$ > $Ph(CH_2)_7$ > $Ph(CH_2)_8$ > C1-C18

| 117 | $CH_2=CH(CH_2)_7$ | 0.00015 ±0.00001 | 118 | $HC{\equiv}C(CH_2)_7$ | 0.00018 ±0.00002 |
| 119 | ~~~=~~~ | | | | 0.00014 ±0.00002 |

| First Generation Inhibitors | IC$_{50}$ FAAH | |
|---|---|---|
| 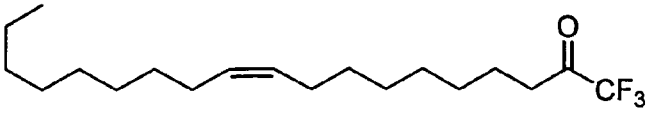 | 41 | 5 µM |
| 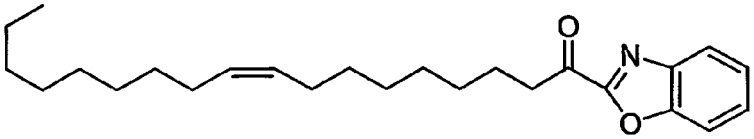 | 83 | 10 µM |
| 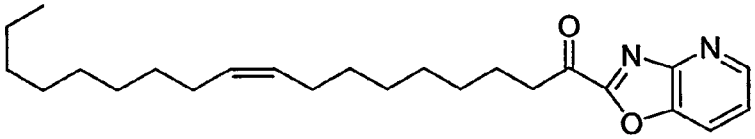 | 89 | 0.044 µM |
| 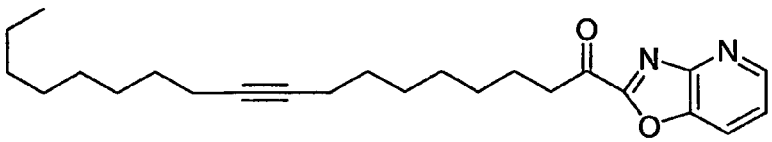 | 119 | 0.007 µM |
| 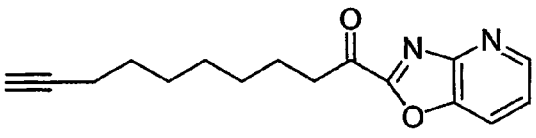 | 118 | 0.0025 µM |
| 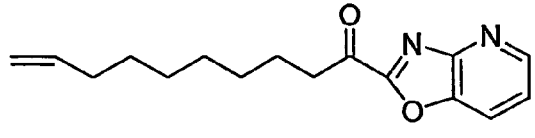 | 117 | 0.0035 µM |
| 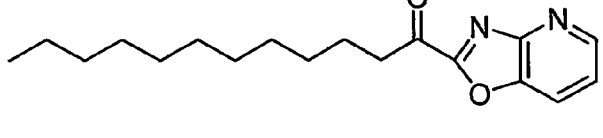 | 104 | 0.0029 µM |
| 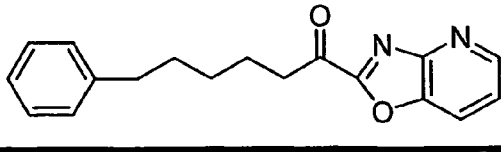 | 53 | 0.001 µM |
Figure 8

| Second Generation Inhibitors | | IC$_{50}$ FAAH |
|---|---|---|
| 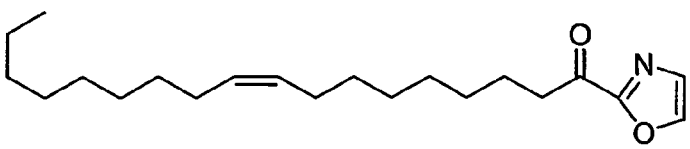 | 70 | 2.3 µM |
| 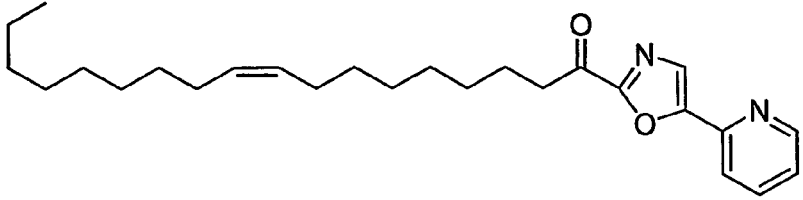 | 143 | 0.15 µM |
| 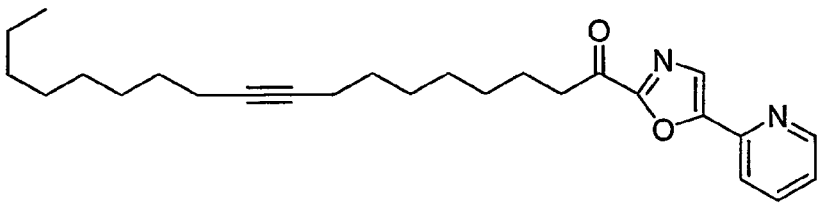 | 205 | 0.05 µM |
| 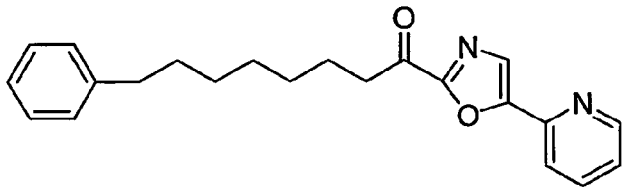 | 201 | 0.01 µM |
Figure 9

Ham, N. K.; Gramer, C. J.; Anderson, B. A. *Tetrahedron Lett.* 1995, *36*, 9453.
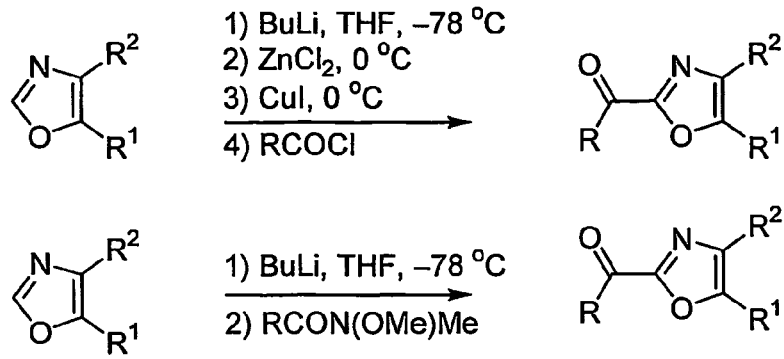
Boger, D. L. et al. *Proc. Natl. Acad. Sci. USA* 2000, *97*, 5049.
Van Leusen, A. M.; Hoogenboom, B. E.; Siderius, H. *Tetrahedron Lett.* 1972, 2369.
Saikachi, H.; Kitagawa, T.; Sasaki, H.; Van Leusen, A. M.
*Chem. Pharm. Bull.* 1979, *27*, 793.
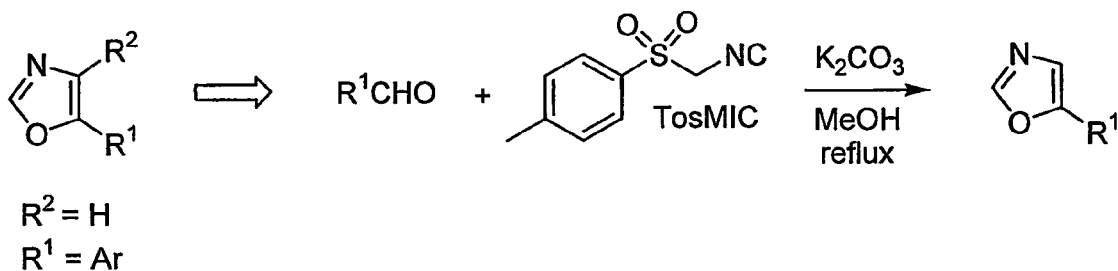
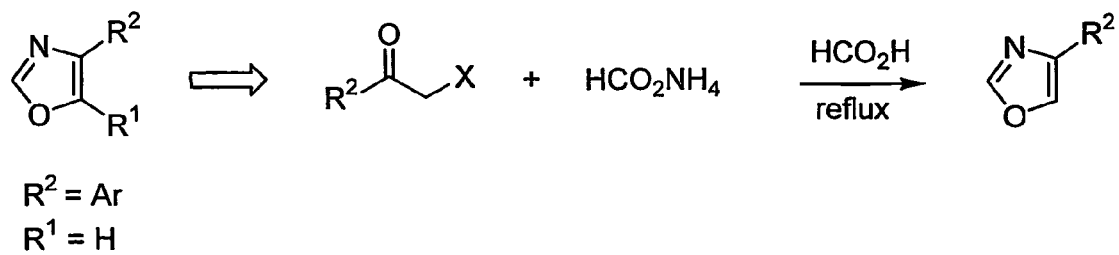
Giardina, G. A.; Sarau, H. M.; Farina, C.; Medhurst, A. D.; Grugni, M.; Raveglia, L. F.; Schmidt, D. B.; Rigolio, R.; Luttmann, M.; Vecchieti, V.; Hay, D. W. P. *J. Med. Chem.* 1997, *40*, 1794.
Figure 10

Alpha-functionalization of the carbonyl-containing tail
Fluorine
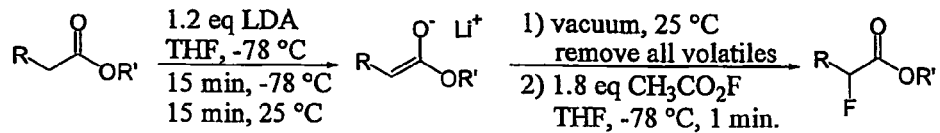
Rozen, S.; Brand, M. *Synthesis* 1985, 665-667.
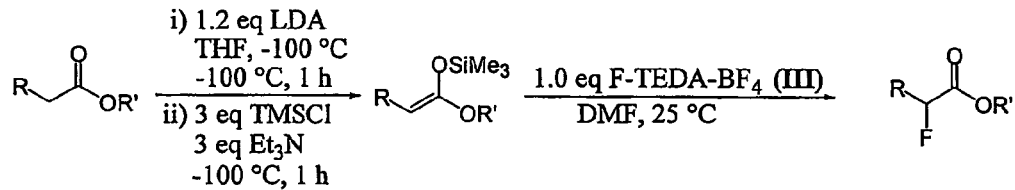
Lal, G. S. *J. Org. Chem.* 1993, *58*, 2791-2796.
α-Chiral Fluorine
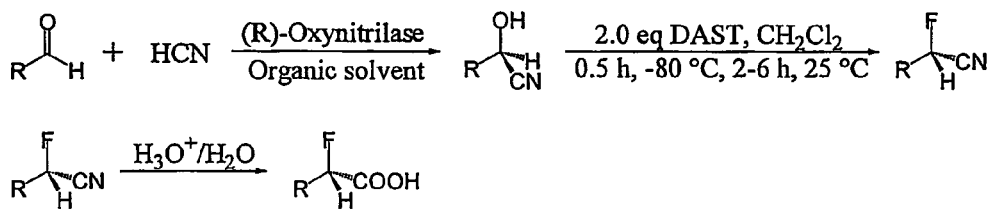
Stelzer, U.; Effenberger, F. *Tetrahedron: Asymmetry* 1993, *4*, 161-164.
Hydroxyl
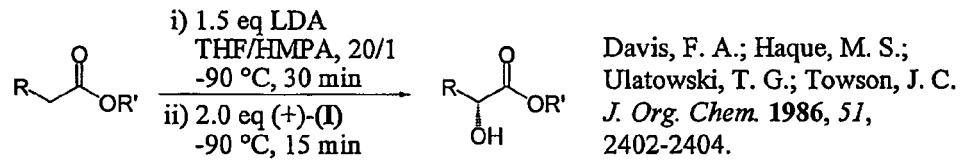
Davis, F. A.; Haque, M. S.; Ulatowski, T. G.; Towson, J. C. *J. Org. Chem.* 1986, *51*, 2402-2404.
Trifluoromethyl
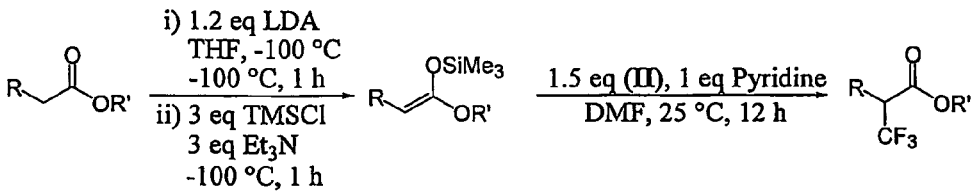
Umemoto, T.; Ishihara, S. *J. Am. Chem. Soc.* 1993, *115*, 2156-2164.
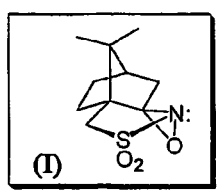
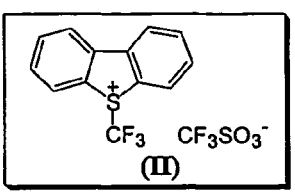
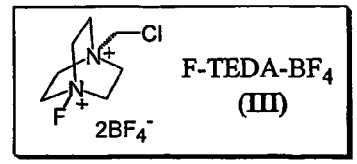
Figure 15

Alpha-functionalization of the carbonyl-containing tail
Chlorine
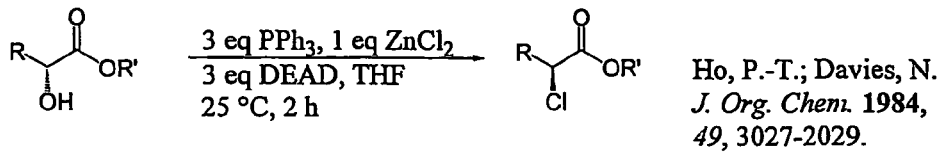
Ho, P.-T.; Davies, N. *J. Org. Chem.* 1984, *49*, 3027-2029.
α-Alkyl-α-hydroxy
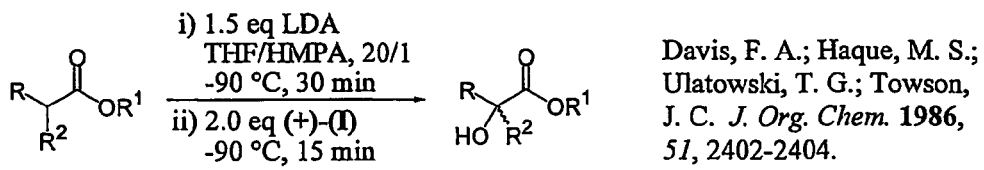
Davis, F. A.; Haque, M. S.; Ulatowski, T. G.; Towson, J. C. *J. Org. Chem.* 1986, *51*, 2402-2404.
α-Hydroxy-α-trifluoromethyl-
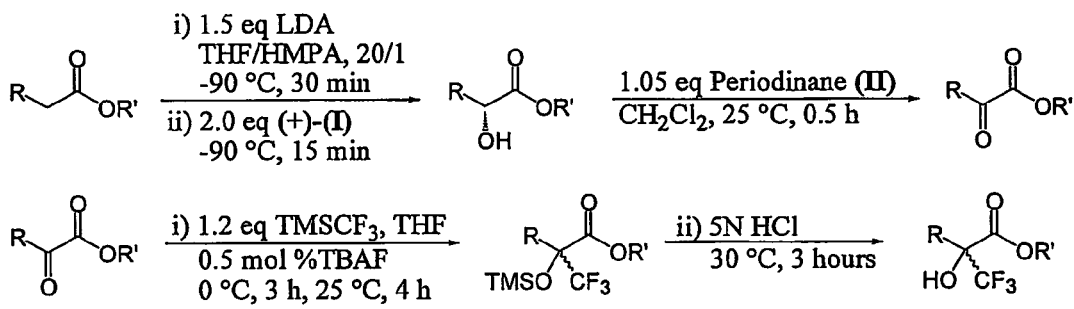
Davis, F. A.; Haque, M. S.; Ulatowski, T. G.; Towson, J. C. *J. Org. Chem.* 1986, *51*, 2402-2404.
Dess, D. B.; Martin, J. C. *J. Org. Chem.* 1983, *83*, 4155-4156.
Ramaiah, P.; Prakash, G. K. S. *Synlett* 1991, 643-644.
α-Alkyl-α-fluoro
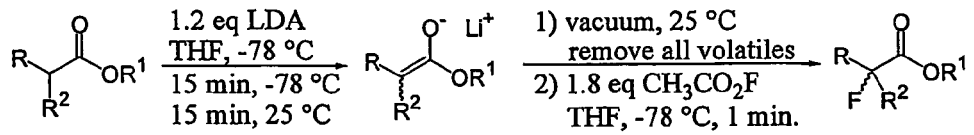
Rozen, S.; Brand, M. *Synthesis* 1985, 665-667.
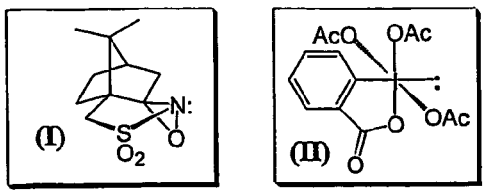
Figure 16

INHIBITORS OF FATTY ACID AMIDE HYDROLASE

TECHNICAL FIELD

The present invention relates to inhibitors of fatty acid hydrolase. More particularly, the invention relates to inhibitors of fatty acid hydrolase of the type having a heterocyclic head group attached to a tail region.

BACKGROUND

Fatty acid amide hydrolase (FAAH) is an integral membrane protein that hydrolyzes a wide range of oleyl and arachidonyl amides, the CB1 agonist 2-arachidonylglycerol, the related 1-arachidonylglycerol and 1-oleylglycerol, and methyl arachidonate, illustrating a range of bioactive fatty acid amide or ester substrates. (W. Lang, et al., (1999) *J. Med. Chem.* 42, 896-902; S. K. Goparaju, et al., (1998) *FEBS Lett.* 442, 69-73; Y. Kurahashi, et al., (1997) *Biochem. Biophys. Res. Commun.* 237, 512-515; and T. Bisogno, et al., (1997) *Biochem. J.* 322,671. Di Marzo, V., T. Bisogno, et al., (1998) *Biochem. J.* 331,15-19). The distribution of FAAH in the CNS suggests that it also degrades neuromodulating fatty acid amides at their sites of action and is intimately involved in their regulation (E. A. Thomas, et al., (1997) *J. Neurosci. Res.* 50, 1047-1052). Although a range of fatty acid primary amides are hydrolyzed by the enzyme, FAAH appears to work most effectively on arachidonyl and oleyl substrates (B. F. Cravaft, et al., (1996) *Nature* 384, 83-87; and D. K. Giang, et al., (1997) *Proc. Natl. Acad. Sci. USA* 94, 2238-2242). FAAH was referred to as oleamide hydrolase and anandamide amidohydrolase in early studies.

A class of FAAH inhibitor represented by the formula A-B—C has been disclosed by Dale Boger (U.S. Pat. No. 6,462,054). In this formula, A is an α-keto heterocyclic pharmacophore for inhibiting the fatty acid amide hydrolase; B is a chain for linking A and C, said chain having a linear skeleton of between 3 and 9 atoms selected from the group consisting of carbon, oxygen, sulfur, and nitrogen, the linear skeleton having a first end and a second end, the first end being covalently bonded to the α-keto group of A, with the following proviso: if the first end of said chain is an α-carbon with respect to the α-keto group of A, then the α-carbon is optionally mono- or bis-functionalized with substituents selected from the group consisting of fluoro, chloro, hydroxyl, alkoxy, trifluoromethyl, and alkyl; and C is a binding subunit for binding to FAAH and enhancing the inhibition activity of said α-keto heterocyclic pharmacophore, said binding subunit having at least one π-unsaturation situated within a π-bond containing radical selected from a group consisting of aryl, alkenyl, alkynyl, and ring structures having at least one unsaturation, with or without one or more heteroatoms, said bind subunit being covalently bonded to the second end of the linear skeleton of B, the π-unsaturation within the π-bond containing radical being separated from the α-keto group of A by a sequence of no less than 4 and no more than 9 atoms bonded sequentially to one another, inclusive of said linear skeleton.

What is needed are FAAH inhibitors having a head group attached to a tail region, the head group having one or more heterocycles for achieving enhanced activity with respect to the inhibition of fatty acid amide hydrolase.

SUMMARY

The invention is directed to improved competitive inhibitors of FAAH that employ an α-keto heterocyclic pharmacophore and a binding subunit having a π-unsaturation. The α-keto heterocyclic pharmacophore and a binding subunit are attached to one another, preferably by a hydrocarbon chain. The improvement lies in the use of a heterocyclic pharmacophore selected from oxazoles, oxadiazoles, thiazoles, and thiadiazoles that include alkyl or aryl substituents at their 4 and/or 5 positions. The improved competitive inhibitors of FAAH display enhanced activity over conventional competitive inhibitors of FAAH.

One aspect of the invention is directed to an inhibitor of fatty acid amide hydrolase represented by the following formula:

A-B—C.

In the above formula, A is an inhibition subunit, B is a linkage subunit, and C is a binding subunit.

The inhibition subunit A is an α-keto heterocyclic pharmacophore for inhibiting the fatty acid amide hydrolase. The α-keto heterocyclic pharmacophore being represented by the following formula:

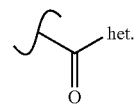

In the above formula, "het" is represented by the following structure:

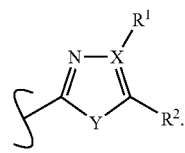

In the above structure, X is selected from the group consisting of carbon and nitrogen; Y is selected from the group consisting of oxygen and sulfur; $R^1$ and $R^2$ are radicals independently selected from the group consisting of hydrogen, C1-C6 alkyl, aromatic ring, and heteroaromatic ring. In a preferred embodiment, $R^1$ and $R^2$ are radicals independently selected from the group consisting of hydrogen, C1-C6 alkyl, and radicals represented by the following structures:

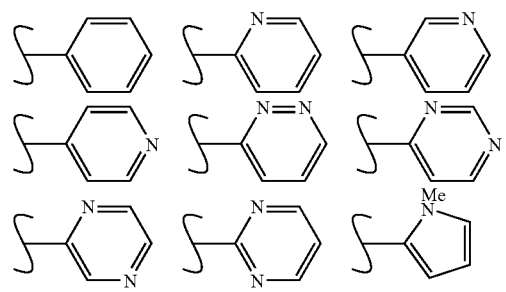

-continued

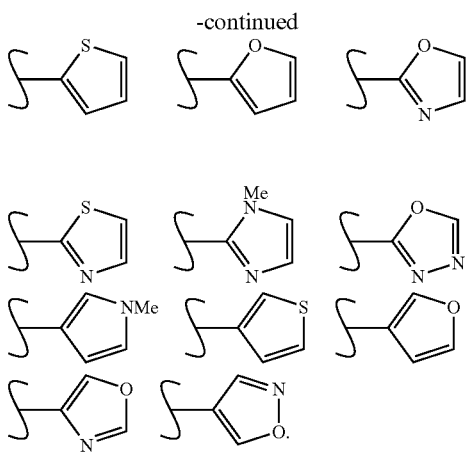

However, there is are two provisos, viz., 1.) $R^1$ and $R^2$ cannot both be hydrogen; and 2.) if X is nitrogen, $R^1$ is absent.

The linkage subunit B is a chain for linking the inhibition subunit A and the binding subunit C and for enabling the binding subunit C to bind to the binding region on the fatty acid amide hydrolase while the inhibition subunit A simultaneously inhibits the fatty acid amide hydrolase. The chain has a linear skeleton of between 3 and 9 atoms selected from the group consisting of carbon, oxygen, sulfur, and nitrogen, the linear skeleton having a first end and a second end, the first end being covalently bonded to the α-keto group of A. However, there is a proviso that, if the first end of said chain is an α-carbon with respect to the α-keto group of the inhibition subunit A, then the α-carbon is optionally mono- or bis-functionalized with substituents selected from the group consisting of fluoro, chloro, hydroxyl, alkoxy, trifluoromethyl, and alkyl.

The binding subunit C is a π-bond containing radical having a π-unsaturation. The binding subunit C is selected from a group consisting of aryl, alkenyl, alkynyl, and ring structures having at least one unsaturation, with or without one or more heteroatoms. The binding subunit C is covalently bonded to the second end of the linkage subunit B. The π-unsaturation within the π-bond containing radical is separated from the α-keto group of A by a sequence of no less than 3 and no more than 9 atoms bonded sequentially to one another, inclusive of the linear skeleton, for enabling the π-unsaturation to bind to the binding region of the fatty acid amide hydrolase while the inhibition subunit A inhibits the fatty acid amide hydrolase. However, there is a proviso that C is optionally C1-C10 alkyl.

In a further preferred embodiment, "het" of the α-keto heterocyclic pharmacophore is selected from the following group:

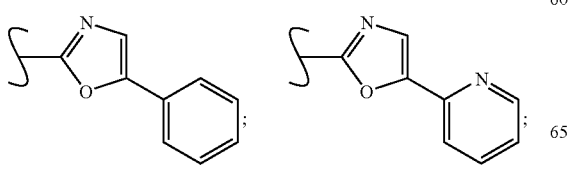

-continued

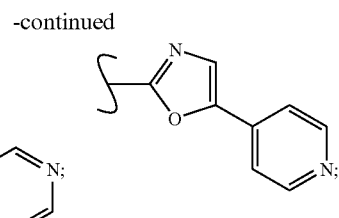

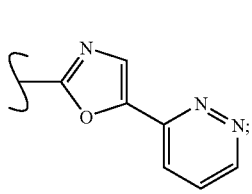

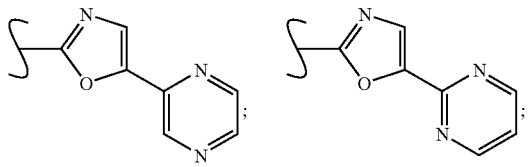

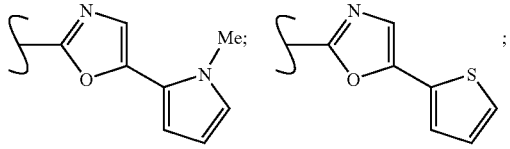

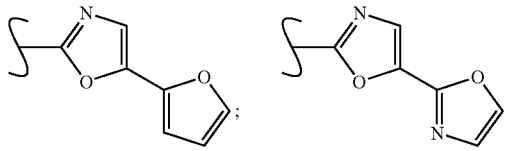

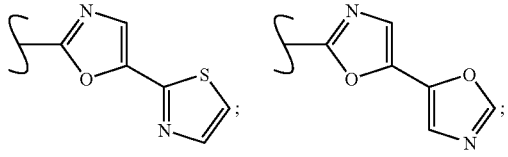

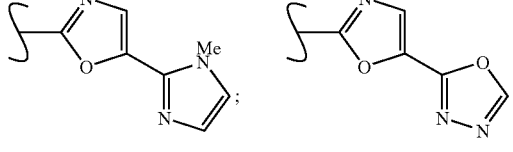

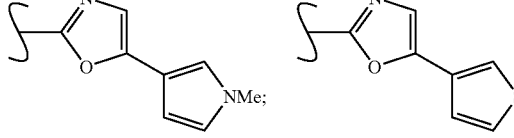

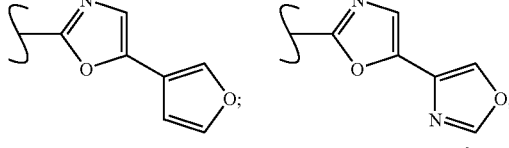

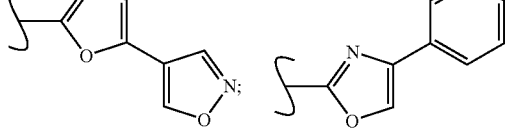

-continued

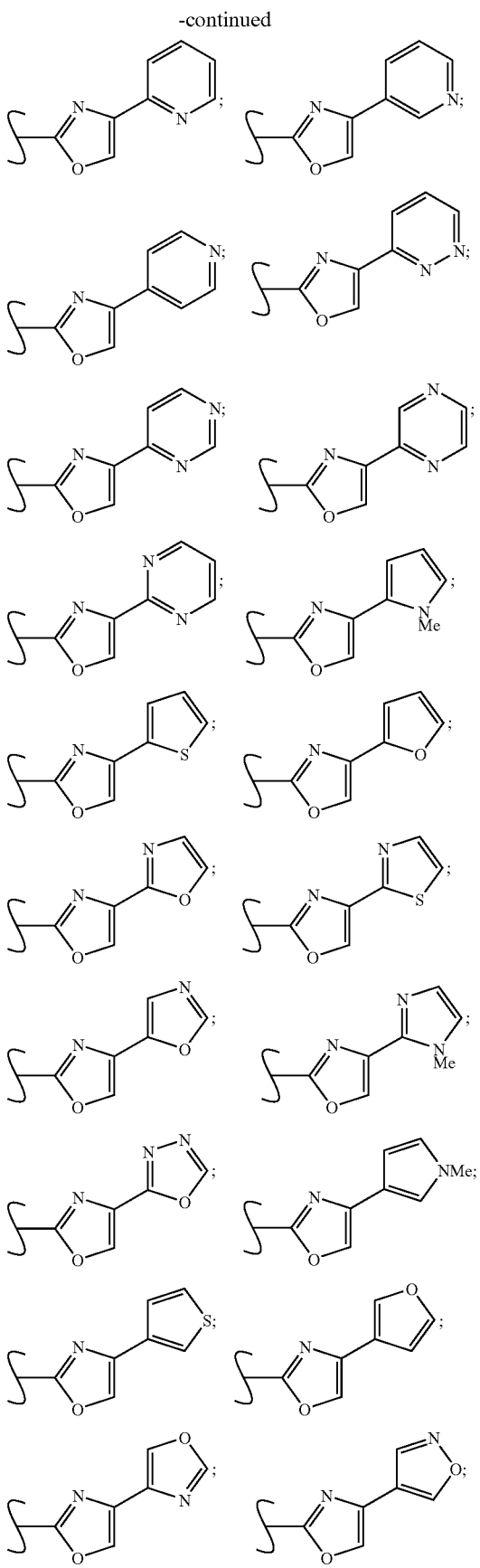

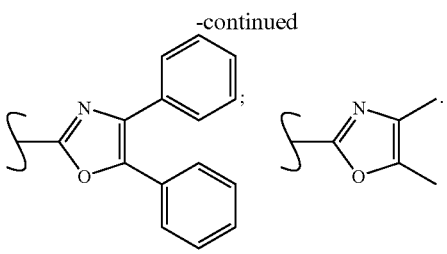

In a further preferred embodiment, the inhibitor of fatty acid amide hydrolase is represented by the following structure:

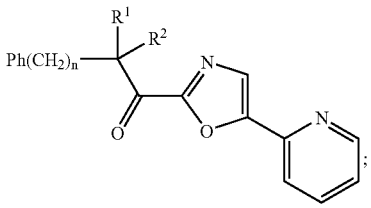

In the above structure, $R^1$ and $R^2$ are independently selected from the group consisting of hydrogen, fluoro, chloro, hydroxyl, alkoxy, trifluoromethyl, and alkyl; and "n" is an integer between 2 and 8.

A further aspect of the invention is directed to processes for inhibiting fatty acid amide hydrolase. The process employs the step of contacting the fatty acid amide hydrolase with an inhibiting concentration of an inhibitor of the type described above. Upon contacting the fatty acid amide, the binding subunit C of the inhibitor binds to the binding region of the fatty acid amide hydrolase for enhancing the inhibition activity of the inhibitor.

BRIEF DESCRIPTION OF FIGURES

FIG. 1 illustrates two tables that list the $K_i$'s for the various compounds tested.

FIG. 2 is a continuation of the second table of FIG. 1 that lists the $K_i$'s for the 4- and 5-heteroaryl substituted α-keto oxazole inhibitors of FAAH.

FIG. 3 illustrates a table of the $K_i$'s of α-keto oxazolopyridine inhibitors of FAAH.

FIG. 5 illustrates the aryl-substituted heterocycles 206 and 207 and their method of synthesis from either the 4- or 5-bromo compounds.

FIG. 6 illustrates a table that shows the change in $K_i$'s of the compounds by the presence or absence of a double bond in the C18 tail of α-keto heterocycle inhibitors of FAAH.

FIG. 8 illustrates a table that shows first generation inhibitors and their $IC_{50}$'s with FAAH.

FIG. 9 illustrates a table that shows second generation inhibitors and their $IC_{50}$'s with FAAH.

FIG. 10 illustrates a series of reactions that disclose how the substituted oxazole inhibitors are synthesized.

FIG. 15 illustrates how the ester is functionalized at the alpha position with fluorine, hydroxyl and trifluoromethyl groups.

FIG. 16 illustrates the methods by which chlorine, alpha-alkyl-alpha-hydroxyl, alpha-alkyl-alpha-trifluoromethyl, and alpha-alkyl-alpha-fluoro groups may be added to an ester.

DETAILED DESCRIPTION

Figure 4:
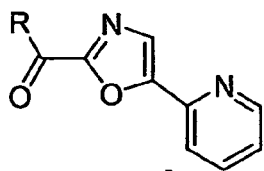
FIG. 4 illustrates a table showing the systematic variation in the side chain and its effects on the activity of the compounds listed. An exemplary head group is used in this series.

Improved competitive inhibitors of FAAH were developed employing an α-keto heterocyclic pharmacophore and a binding subunit having a π-unsaturation. The α-keto heterocyclic pharmacophore and a binding subunit are attached to one another, preferably by a hydrocarbon chain. The improvement lies in the use of a heterocyclic pharmacophore selected from oxazoles, oxadiazoles, thiazoles, and thiadiazoles that include alkyl or aryl substituents at their 4 and/or 5 positions. The improved competitive inhibitors of FAAH display enhanced activity over conventional competitive inhibitors of FAAH which employ non-azole heterocyclic pharmacophores and/or heterocyclic pharmacophores that lack aryl or alkyl substituents.

The improved competitive inhibitors of FAAH disclosed herein confirm that incorporation of an unsaturation into the fatty acid chain increases inhibitor potency. The incorporation of a benzene ring proved to be particularly effective. Similarly, the electrophilic carbonyl was confirmed to be required for potent enzyme inhibition with respect to the competitive inhibitors of FAAH disclosed herein.

Methods

Inhibition Studies:

All enzyme assays were performed at 20-23° C. using a solubilized liver plasma membrane extract containing FAAH in a reaction buffer of 125 mM Tris, 1 mM EDTA, 0.2% glycerol, 0.02% Triton X-100, 0.4 mM HEPES, pH 9.0 buffer (M. P. Patricelli, et al., (1998) *Bioorg. Med. Chem. Lett.* 8, 613-618; and J. E. Patterson, et al., (1996) *J. Am. Chem. Soc.* 118, 5938-5945). The initial rates of hydrolysis were monitored by following the breakdown of $^{14}$C-oleamide to oleic acid as previously described (B. F. Cravatt, et al., (1995) *Science* 268, 1506-1509; and M. P. Patricelli, et al., (1998) *Bioorg. Med. Chem. Lett.* 8, 613-618). The inhibition was reversible, non time-dependent and linear least squares fits were used for all reaction progress curves and $R^2$ values were consistently >0.97. $IC_{50}$ values were determined from the inhibition observed at 3-5 different inhibitor concentrations (from three or more trials at each inhibitor concentration) using the formula $IC_{50}=[I]/[(K_0/K_i)-1]$, where $K_0$ is the control reaction rate without inhibitor and $K_i$ is the rate with inhibitor at concentration [I] (K. Conde-Frieboes, et al., (1996) *J. Am. Chem. Soc.* 118, 5519-5525). $K_i$ values were determined by the Dixon method (x-intercepts of weighted linear fits of [I] versus 1/rate plots at constant substrate concentration, which were converted to $K_i$ values using the formula $K_i=-x_{int}/[1+[S]/K_m]$). Previous work demonstrated the rat and human enzyme are very homologous (84%), exhibit near identical substrate specificities, and incorporate an identical amidase consensus sequence and SH3 binding domain suggesting the observations made with rat FAAH will be similar if not identical to those of human FAAH (B. F. Cravatt, et al., (1996) *Nature* 384, 83-87; and D. K. Giang, et al., (1997) *Proc. Natl. Acad. Sci. USA* 94, 2238-2242).

Detailed Description of Figures:

FIG. 1 illustrates two tables that list the $K_i$'s for the various compounds tested. The first table shows that the oxazole and oxadiazole are over 1000 times more potent than the thiazole. Interestingly, the potency is very nearly recovered by the substitution of another nitrogen in the thiadiazole heterocycle. The second table shows the variations in the heterocycle in the 4- and 5-positions of the oxazole head group and its effect on $K_i$. FIG. 2 is a continuation of the second table in FIG. 1. One trend seen with the data is the increase in activity with nitrogen-containing heterocycles.

FIG. 3 illustrates a table of the $K_i$'s of α-keto oxazolopyridine inhibitors of FAAH. The clear trends are noted below the table. As seen in FIG. 2 with the 4- and 5-aryl-substituted oxazole headgroup compounds, the introduction of a basic nitrogen in the ring leads to greatly enhanced activity. There is no large change in $K_i$ with the change in nitrogen position.

FIG. 4 illustrates a table showing the modifications in the fatty acid side chain and the effects on $K_i$. The trend is slightly different here than that of the oxazolopyridine inhibitor tested earlier. A saturated dodecanoyl group on this 5-(2-pyridyl)-substituted oxazole gave a lower $K_i$ than the favored alkylphenyl side chain. The difference between compounds 185 and 200 is only a factor of two.

FIG. 5 illustrates compounds 206 and 207 and how a palladium-catalyzed cross-coupling reaction is used to synthesize them. The Suzuki coupling is accomplished by using catalytic palladium (0) dibenzylidene acetone in the presence of base and the desired aryl or heteroaryl boronic acid (Miyaura, N.; Suzuki, A. *Chem. Rev.* 1995, 95, 2857-2483).

FIG. 6 illustrates a table that shows the change in $K_i$'s of the compounds by the presence or absence of a double bond in the C18 tail of α-keto heterocycle inhibitors of FAAH. The first three compounds show that the unsaturation in the chain is important for binding to such an extent that the binding constant is five-fold greater for the fully saturated chain. Essentially the same result is observed for the next two head groups.

Figure 7:
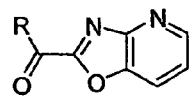
FIG. 7 illustrates a table that shows the effect of modifying the fatty acid side chain of α-keto oxazolopyridine inhibitors of FAAH on the $K_i$'s of the compounds.

FIG. 7 illustrates a table that shows the effect of modifying the fatty acid side chain of α-keto oxazolopyridine inhibitors of FAAH on the $K_i$'s of the compounds. This table compares the various hydrocarbon tail groups with each other and the general trends are summarized in the lines on the bottom of the chart. The best saturated chains are those with between 8 and 12 carbons. The phenyl-containing side chains are about 3 times as potent as the saturated side chains with this head group. The best $K_i$ was 200 pM for this series of compounds.

FIG. 8 illustrates a table that shows first generation inhibitors and their $IC_{50}$'s with FAAH. The value for the $IC_{50}$ is approximately 10 times larger than the corresponding $K_i$'s for this enzyme. A trifluoromethyl ketone is included for comparison with the designed inhibitors. The $IC_{50}$'s correspond well to the $K_i$'s of the compounds. Again, compound 118 has both the lowest $IC_{50}$ and $K_i$.

FIG. 9 illustrates a table that shows second generation inhibitors and their $IC_{50}$'s with FAAH. The second generation inhibitors show more variation in their $IC_{50}$'s compared to their corresponding $K_i$'s.

FIG. 10 illustrates a series of reactions that illustrate how the substituted, oxazole inhibitors are synthesized. The first reaction at the top of the page shows how the 2-position on the oxazole is acylated. The oxazole is first lithiated with n-butyllithium, transmetallated with zinc chloride, the cuprate is formed by the addition of copper(I) iodide and then the cuprate is acylated with the acid chloride. The detailed procedure is described for compound 162 in the experimental section. The second method for the formation of the 2-acyl oxazoles is a standard lithiation and then acylation with the Weinreb amide. Compound 144 was synthesized by this method as outlined in the experimental section. The remaining two reactions show the retrosynthesis for the 4- or 5-substituted heterocycle. In the last reaction, X is a halogen or some other leaving group.

Figure 11:
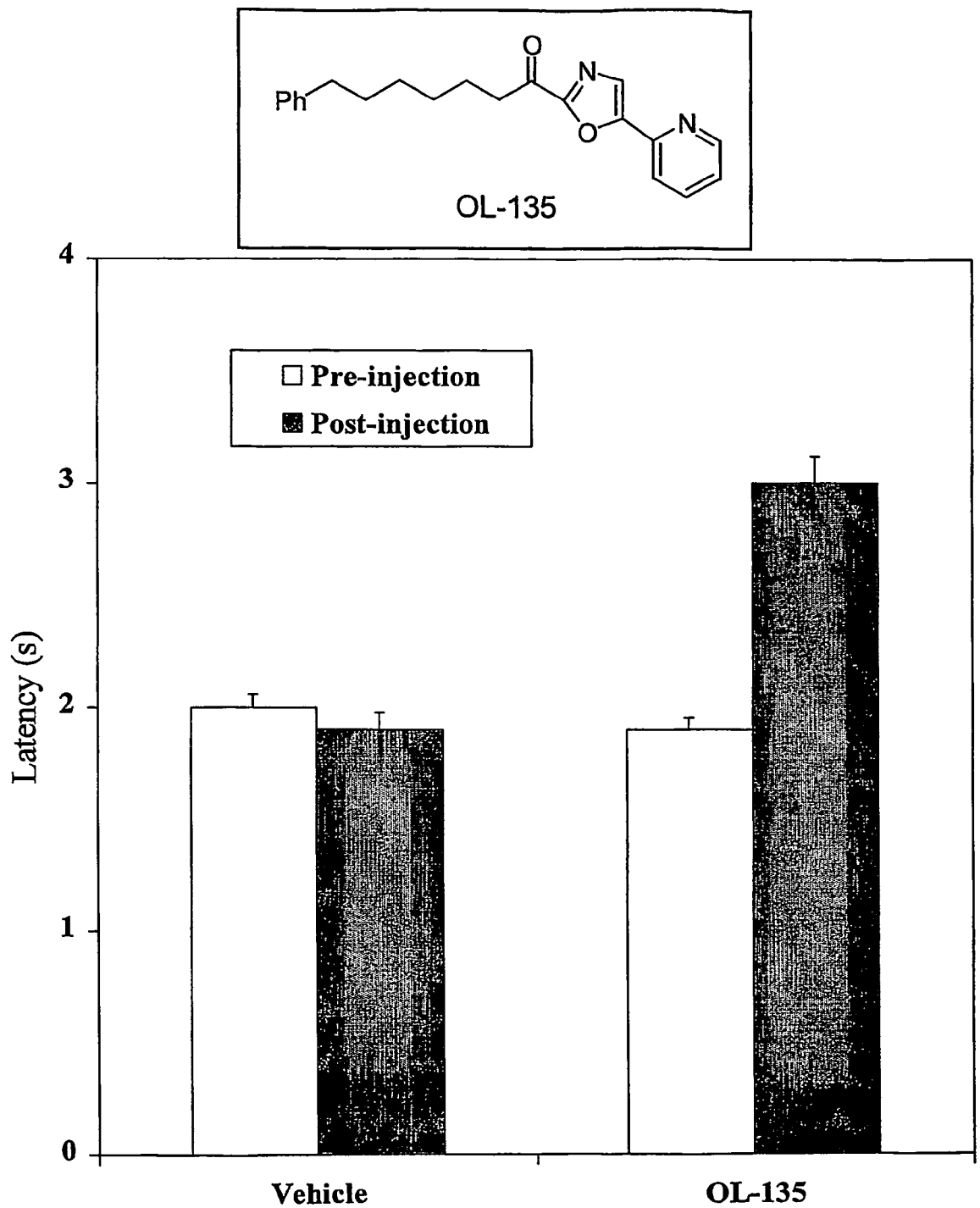
FIG. 11 illustrates a bar graph showing the reduced thermal pain responses 60 minutes following the injection of OL-135 (10 mg/kg, i.p.).

FIG. 11 illustrates a bar graph showing the reduced thermal pain responses 60 minutes following the injection of OL-135 (10 mg/kg, i.p.). This test is the tail withdrawal test and there is no effect with the vehicle while there is marked delay after administration of the OL-135. [$p<0.001$; N=12 mice per group; results shown as means ±S.E.]

Figure 12:
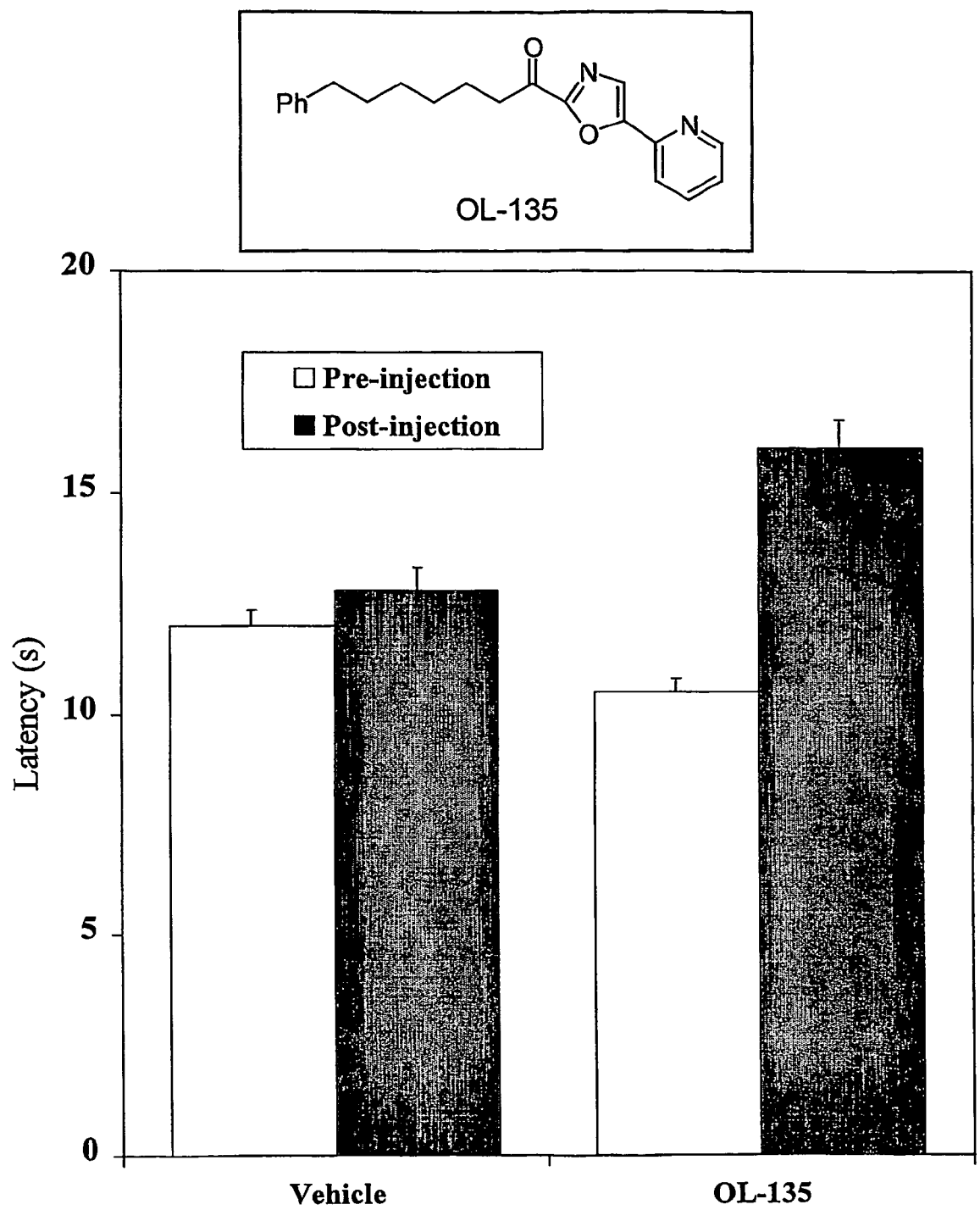
FIG. 12 illustrates a bar graph showing the reduced thermal pain responses 60 minutes following the injection of OL-135 (10 mg/kg, i.p.).

FIG. 12 illustrates a bar graph showing the reduced thermal pain responses 60 minutes following the injection of OL-135 (10 mg/kg, i.p.). This test is the hot plate test and there is no effect with the vehicle and there is some delay after administration of the OL-135. [$p<0.01$; N=12 mice per group; results shown as means ±S.E.]

Figure 13:
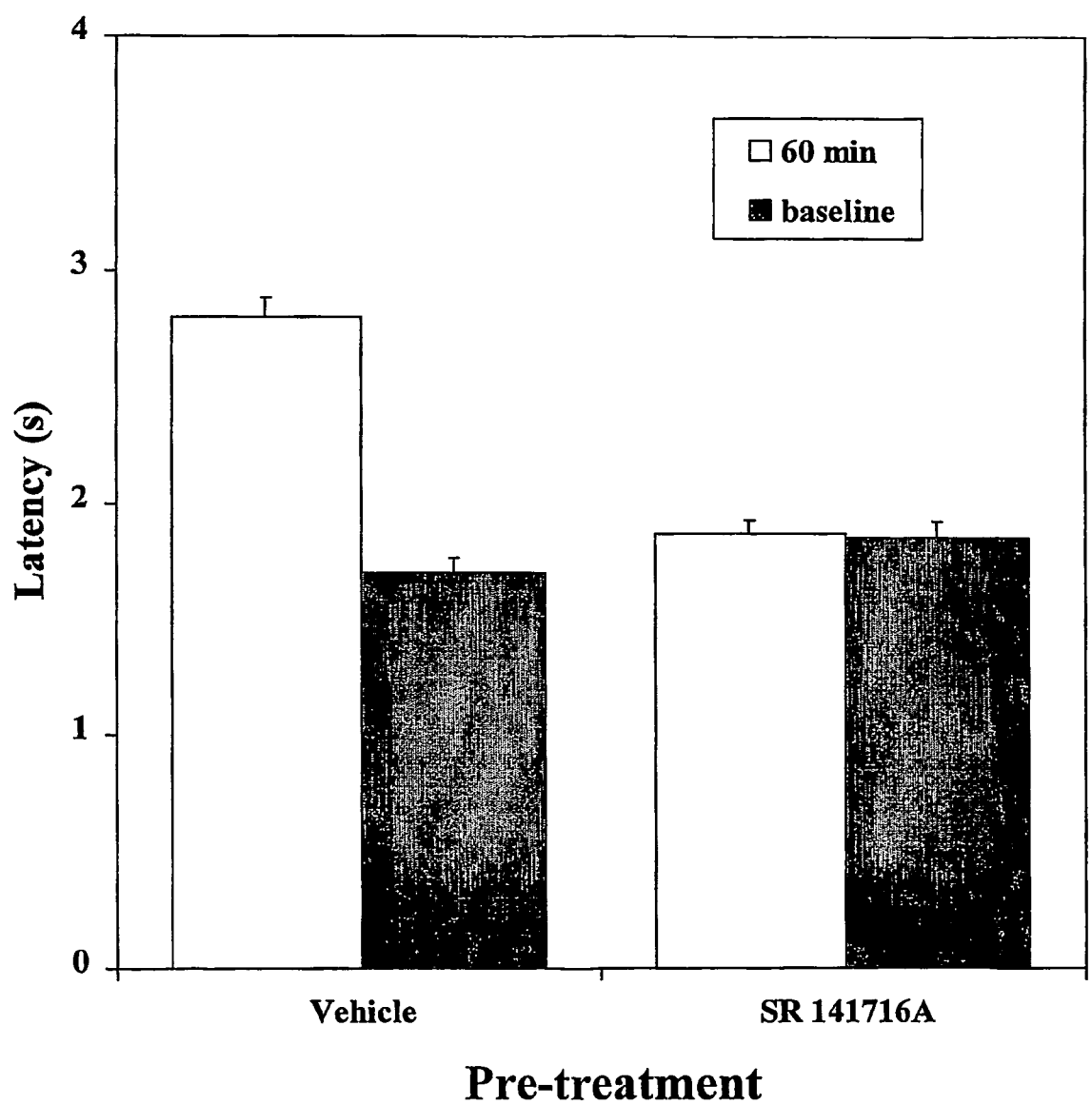
FIG. 13 illustrates a bar graph that shows SR 141716A blocking the analgesic effects of OL-135 in the tail immersion test.

FIG. 13 illustrates a bar graph that shows SR 141716A blocking the analgesic effects of OL-135 in the tail immersion test. The mice received an i.p. injection of vehicle or SR 141716A (3 mg/kg); 10 minutes later all subjects were given OL-135 (10 mg/kg, i.p.) and then evaluated in the tail immersion test one hour after the second injection. ($p<0.001$ for OL-135-treated mice that were pretreated with vehicle versus either their pre-injection baseline latencies or OL-135 treated mice that were pretreated with SR 141716A.) Results are shown as means ±S. E. N=6 mice/group.

Figure 14:
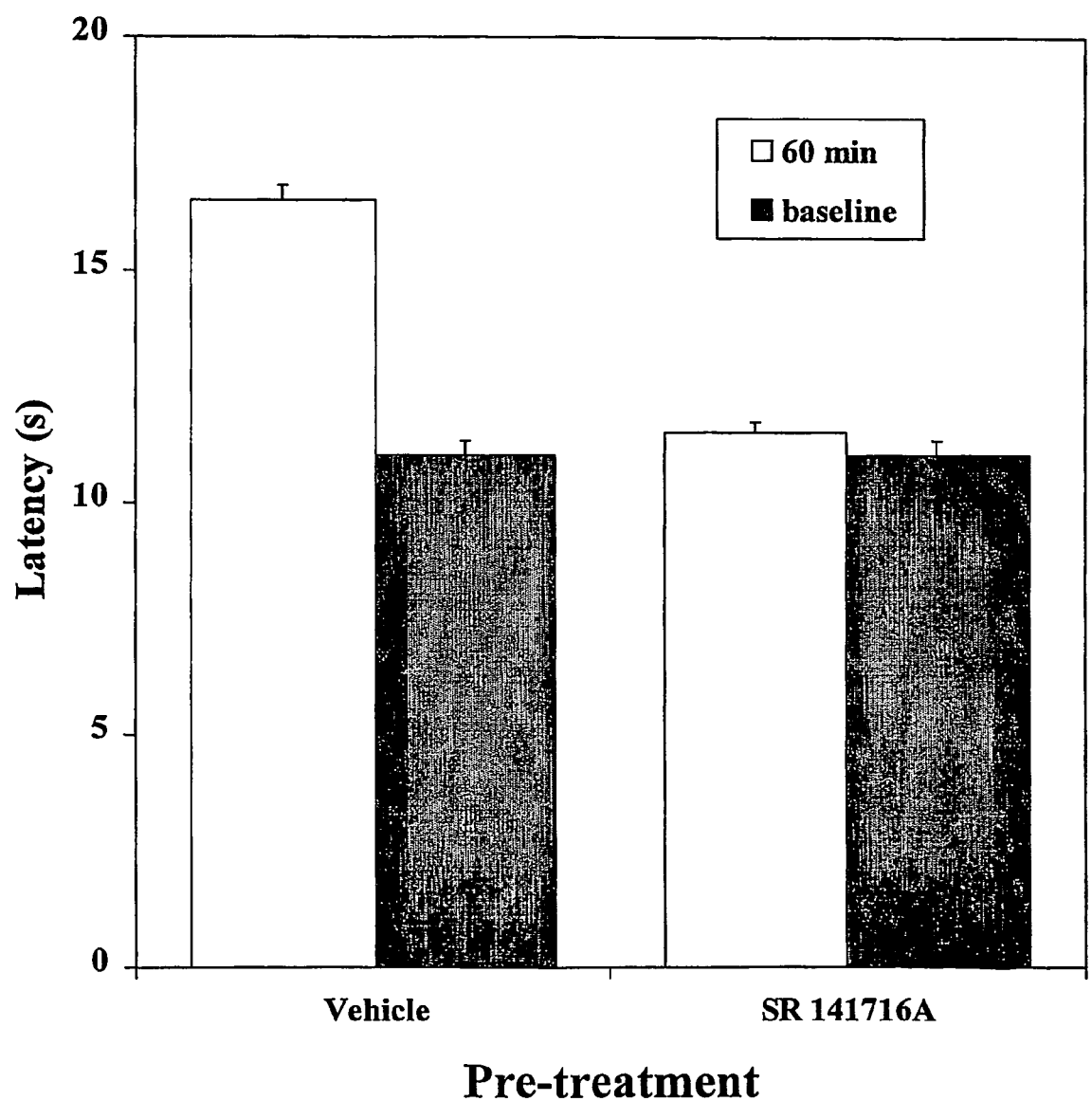
FIG. 14 illustrates a bar graph that shows SR 141716A blocking the analgesic effects of OL-135 in the hot plate test.

FIG. 14 illustrates a bar graph that shows SR 141716A blocking the analgesic effects of OL-135 in the hot plate test. The mice received an i.p. injection of vehicle or SR 141716A (3 mg/kg); 10 minutes later all subjects were given OL-135 (10 mg/kg, i.p.) and then evaluated in the hot plate test one hour after the second injection. [$p<0.001$ for OL-135-treated mice that were pretreated with vehicle versus either their pre-injection baseline latencies or OL-135 treated mice that were pretreated with SR 141716A. Results are shown as means ±S. E. N=6 mice/group.]

FIG. 15 illustrates how the ester is functionalized at the alpha position with fluorine, hydroxyl and trifluoromethyl groups. An asymmetric method for making a chiral alpha-fluoro ester is given, but one familiar with the art will know how to accomplish making the trifluoromethyl derivative in an asymmetric fashion. These methods assume that any functional groups present in "R" have suitable protection.

FIG. 16 illustrates the methods by which chlorine, alpha-alkyl-alpha-hydroxyl, alpha-alkyl-alpha-trifluoromethyl, and alpha-alkyl-alpha-fluoro groups may be added to an ester. Depending on what "R" is, some of these esters or the corresponding acids may be commercially available. A Mitsunobu reaction is done to obtain the alpha-chloro compound from the corresponding alpha-hydroxy ester. An asymmetric hydroxylation of an enolate of an alpha-alkyl ester is accomplished by using an asymmetric oxaziridine (I). The last two products in this figure are obtained as racemates.

Experimental 1-([1,3,4]Oxadiazol-2-yl)octadec-9-en-1-one. (140) A suspension of the Dess-Martin periodinane (1.2 equiv, 0.025 mmol, 11 mg) in anhydrous $CH_2Cl_2$ (0.5 mL) was treated with a solution of 1-([1,3,4]oxadiazol-2-yl)octadec-9-en-1-ol (7 mg, 0.021 mmol) in anhydrous $CH_2Cl_2$ (0.5 mL) at rt under $N_2$. After 6 h the suspension was diluted with $Et_2O$ (10 mL), and poured into a solution of $Na_2S_2O_3$ (77 mg) in saturated aqueous $NaHCO_3$ (6.5 mL). The mixture was stirred at rt for 1 h and the layers were separated. The ethereal layer was washed with saturated aqueous $NaHCO_3$ (1×10 mL) and $H_2O$ (1×10 mL), dried ($MgSO_4$), filtered and evaporated. Flash chromatography ($SiO_2$, 1.5 cm×15 cm, 2% MeOH—$CH_2Cl_2$) afforded 1-([1,3,4]oxadiazol-2-yl)octadec-9-en-1-one (140) (5 mg, 0.016 mmol, 75% yield) as a dark yellow oil: $^1$H NMR ($CDCl_3$, 250 MHz) d 9.34 (s, 1H), 5.42-5.26 (m, 2H), 3.04 (t, J=7.4 Hz, 2H), 2.12-1.87 (m, 4H), 1.82-1.75 (m, 2H), 1.43-1.19 (m, 20H), 0.88 (br t, J=6.8 Hz, 3H); IR ($CDCl_3$)$u_{max}$ 2940, 2860, 1705, 1612, 1547, 1510, 1423, 1380 $cm^{-1}$; MALDI-FTMS (DHB) m/z 335.2689 ($C_{20}H_{34}N_2O_2+H^+$ requires 335.2698).

1-([1,3,4]Thiadiazol-2-yl)octadec-9-en-1-one. (141) A suspension of the Dess-Martin periodinane (1.2 equiv, 0.013 mmol, 14 mg) in anhydrous $CH_2Cl_2$ (0.5 mL) was treated with a solution of 1-([1,3,4]thiadiazol-2-yl)octadec-9-en-1-ol (4 mg, 0.011 mmol) in anhydrous $CH_2Cl_2$ (0.5 mL) at rt under $N_2$. After 10 h the suspension was diluted with $Et_2O$ (10 mL), and poured into a solution of $Na_2S_2O_3$ (40 mg) in saturated aqueous $NaHCO_3$ (3.4 mL). The mixture was stirred at rt for 1 h and the layers were separated. The ethereal layer was washed with saturated aqueous $NaHCO_3$ (1×10 mL) and $H_2O$ (1×10 mL), dried ($MgSO_4$), filtered and evaporated. Flash chromatography ($SiO_2$, 1.5 cm×15 cm, 2% MeOH—$CH_2Cl_2$) afforded 1-([1,3,4]thiadiazol-2-yl)octadec-9-en-1-one (141) (3 mg, 0.008 mmol, 70% yield) as a dark yellow oil: MALDI-FTMS (DHB) m/z 351.2464 ($C_{20}H_{34}N_2OS+H^+$ requires 351.2470).

1-(5-Phenyloxazol-2-yl)-1-oxo-9(Z)-octadecene. (142) This material was prepared from 5-phenyloxazole (Van Leusen, A. M.; et al *Tetrahedron Lett.* 1972, 2369-2372) using the procedure described for 162. Column chromatography ($SiO_2$, 2.5×12 cm, 3% $Et_2O$-hexanes) afforded 142 (192 mg, 0.471 mmol, 72%) as a colorless crystalline powder: mp 32.0° C.; MALDI-FTMS (NBA-NaI) m/z 432.2892 ($C_{27}H_{39}NO_2+Na^+$ requires 432.2873).

1-Oxo-1-[5-(2-pyridyl)oxazol-2-yl]-9(Z)-octadecene. (143) This material was prepared from 5-(2-pyridyl)oxazole (Saikachi, H.; et al. *Chem. Pharm. Bull.* 1979, 27, 793-796) using the procedure described for 162. Column chromatography ($SiO_2$, 2.5×12 cm, 1% MeOH—$CHCl_3$) afforded 143 (64.3 mg, 0.157 mmol, 24%) as a pale yellow oil: MALDI-FTMS (NBA-NaI) m/z 433.2826 ($C_{26}H_{38}N_2O_2+Na^+$ requires 433.2825).

1-Oxo-1-[5-(3-pyridyl)oxazol-2-yl]-9(Z)-octadecene. (144) A solution of BuLi in hexanes (2.5 M, 0.13 mL, 0.325 mmol, 1.05 equiv) was added dropwise to a solution of 5-(3-pyridyl)oxazole (Saikachi, H.; et al. *Chem. Pharm. Bull.* 1979, 27, 793-796) (45 mg, 0.308 mmol, 1.0 equiv) in anhydrous THF (5.0 mL) at −78° C., and the resulting solution was stirred at −78° C. for 10 min. A solution of N-methoxy-N-methyloleoyl amide (100 mg, 0.308 mmol, 1.0 equiv) in anhydrous THF (2.0 mL) was added dropwise to the mixture, and the mixture was warmed to room temperature. After stirring for 16 h, water (15 mL) was added to the mixture, and the mixture was extracted with ethyl acetate (50 mL). The organic layer was washed with saturated aqueous NaCl (20 mL), dried over anhydrous $Na_2SO_4$, filtered, and evaporated.

Chromatography (SiO$_2$, 1.5×12 cm, CHCl$_3$) afforded 144 (40.4 mg, 0.098 mmol, 32% yield) as a colorless crystalline powder: mp 35.5-36.0° C.; MALDI-FTMS (NBA-NaI) m/z 411.3002 (C$_{26}$H$_{38}$N$_2$O$_2$+H$^+$ requires 411.3006).

1-Oxo-1-[5-(4-pyridyl)oxazol-2-yl]-9(Z)-octadecene. (145) This material was prepared from 5-(4-pyridyl)oxazole (Saikachi, H.; et al. *Chem. Pharm. Bull.* 1979, 27, 793-796) using the procedure described for 144. Column chromatography (SiO$_2$, 1.5×12 cm, 3% Et$_2$O-hexanes) afforded 145 (80.8 mg, 0.197 mmol, 64%) as a colorless solid: mp 48.0-49.0° C.; MALDI-FTMS (NBA-NaI) m/z 411.3004 (C$_{26}$H$_{38}$N$_2$O$_2$+H$^+$ requires 411.3006).

1-[5-(1-Methylpyrrol-2-yl)oxazol-2-yl]-1-oxo-9(Z)-octadecene. (150) This material was prepared from 5-(1-methylpyrrol-2-yl)oxazole (Saikachi, H.; et al. *Chem. Pharm. Bull.* 1979, 27, 793-796) using the procedure described for 162. Column chromatography (SiO$_2$, 2.5×12 cm, 10% EtOAc-hexanes) afforded 150 (157 mg, 0.380 mmol, 59%) as a pale red oil: MALDI-FTMS (NBA-NaI) m/z 413.3172 (C$_{26}$H$_{40}$N$_2$O$_2$+H$^+$ requires 413.3163).

1-oxo-1-[5-(2-thienyl)oxazol-2-yl]-9(Z)-octadecene. (151) This material was prepared from 5-(2-thienyl)oxazole (Saikachi, H.; et al. *Chem. Pharm. Bull.* 1979, 27, 793-796) using the procedure described for 162. Column chromatography (SiO$_2$, 2.5×12 cm, 5% Et$_2$O-hexanes) afforded 151 (165 mg, 0.397 mmol, 61%) as a pale yellow oil: MALDI-FTMS (NBA-NaI) m/z 416.2617 (C$_{25}$N$_{37}$NO$_2$S+H$^+$ requires 416.2618).

1-[5-(2-Furyl)oxazol-2-yl]-1-oxo-9(Z)-octadecene. (152) This material was prepared from 5-(2-furyl)oxazole (Saikachi, H.; et al. *Chem. Pharm. Bull.* 1979, 27, 793-796) using the procedure described for 162. Column chromatography (SiO$_2$, 2.5×12 cm, 3% Et$_2$O-hexanes) afforded 152 (177 mg, 0.443 mmol, 68%) as a pale orange oil: MALDI-FTMS (NBA-NaI) m/z 400.2849 (C$_{25}$H$_{37}$NO$_3$+H$^+$ requires 400.2846).

1-Oxo-1-[5-(thiazol-2-yl)oxazol-2-yl]-9(Z)-octadecene. (154) 5-(Thiazol-2-yl)oxazole. Potassium carbonate (690 mg, 5.00 mmol, 1.0 equiv) was added to a solution of 2-thiazolecarboxaldehyde (566 mg, 5.00 mmol, 1.0 equiv) and (p-toluenesulfonyl)methyl isocyanide (TosMIC) (975 mg, 5.00 mmol, 1.0 equiv) in distilled methanol (15 mL) and the mixture was stirred at reflux for 3 h. After cooling to room temperature, the mixture was concentrated under reduced pressure. The residue was diluted with chloroform (70 mL) and washed with water (20 mL). The organic layer was dried over anhydrous Na$_2$SO$_4$, filtered, and evaporated. Chromatography (SiO$_2$, 15 g, hexanes:ether=5:1) afforded 5-(thiazol-2-yl)oxazole (626 mg, 4.11 mmol, 82%) as a pale yellow crystalline powder: $^1$H NMR (CDCl$_3$, 250 MHz) δ 7.96 (s, 1H), 7.90 (d, $_1$H, J=3.3 Hz), 7.67 (s,1H), 7.42 (d, 1H, J=3.3 Hz).

1-Oxo-1-[5-(thiazol-2-yl)oxazol-2-yl]9(Z)-octadecene. This material was prepared from 5-(thiazol-2-yl)oxazole using the procedure described for 162. Column chromatography (SiO$_2$, 2.5×12 cm, 10% Et$_2$O-hexanes) afforded 154 (97.2 mg, 0.233 mmol, 36%) a pale yellow crystalline powder: mp 32.0-32.5° C.; MALDI-FTMS (NBA-NaI) m/z 417.2572 (C$_{24}$H$_{36}$N$_2$O$_2$S+H$^+$ requires 417.2570).

1-Oxo-1-[5-(1-methylimidazol-2-yl)oxazol-2-yl]-9(Z)-octadecene. (155) 5-(1-Methylimidazol-2-yl)oxazole. This material was prepared in 79% yield from 1-methylimidazol-2-carboxaldehyde using the procedure described for 5-(thiazol-2-yl)oxazole. Column chromatography (SiO$_2$, 2.5×12 cm, 1% MeOH—CHCl$_3$) afforded 5-(1-methylimidazol-2-yl)oxazole (586 mg, 3.93 mmol, 79%) a yellow crystalline powder $^1$H NMR (CDCl$_3$, 250 MHz) δ 7.96 (s, 1H), 7.48 (s, 1H), 7.14 (d, 1H, J=1.1 Hz), 6.97 (d, 1H, J=1.1 Hz), 3.86 (s, 3H).

1-Oxo-1-[5-(1-methylimidazol-2-yl)oxazol-2-yl]-9(Z)-octadecene. (155) This material was prepared from 5-(1-methylimidazol-2-yl)oxazole using the procedure described for 162. Column chromatography (SiO$_2$,1.5×12 cm, 50% Et$_2$O-hexanes) afforded 155 (44.6 mg, 0.108 mmol, 17%) a pale orange crystalline powder: mp. 46.0-47.0° C.; MALDI-FTMS (NBA-NaI) m/z 414.3123 (C$_{25}$H$_{39}$N$_3$O$_2$+H$^+$ requires 414.3115).

1-[5-(3-Thienyl)oxazol-2-yl]-1-oxo-9(Z)-octadecene. (158) 5-(3-Thienyl)oxazole. This material was prepared from thiophene-3-carboxaldehyde using the procedure described for 5-(thiazol-2-yl)oxazole (vide supra). Column chromatography (SiO$_2$, 2.5×12 cm, 10% EtOAc-hexanes) afforded 5-(3-thienyl)oxazole (519 mg, 3.43 mmol, 34%) a yellow oil: $^1$H NMR (CDCl$_3$, 250 MHz) δ 7.97 (s,1H), 7.66 (dd,1H, J=2.9 and 1.1 Hz), 7.50 (dd,1H, J=4.9 and 2.9 Hz), 7.32 (s, 1H), 7.10 (d, 1H, J=4.9 and 1.1 Hz).

1-Oxo-1-[54(3-thienyl)oxazol-2-yl]-9(Z)-octadecene. (158) This material was prepared from 5-(3-thienyl)oxazole using the procedure described for 162. Column chromatography (SiO$_2$, 1.5×12 cm, 5% EtOAc-hexanes) afforded 158 (102 mg, 0.244 mmol, 38%) a pale yellow oil: $^1$H NMR (CDCl$_3$, 250 MHz) δ 7.77 (dd, 1H, J=2.6 and 1.5 Hz), 7.43 (dd, 1H, J=5.0 and 2.6 Hz), 7.39 (dd, 1H, J=5.0 and 1.5 Hz), 7.35 (s, 1H), 5.44-5.27 (m, 2H), 3.07 (t, 3H, J=7.5 Hz),2.10-1.93 (m, 4H), 1.84-1.69 (m, 2H), 1.47-1.19 (m, 20H), 0.87 (t, 3H, J=6.6 Hz); IR (film) u$_{max}$ 3109, 3005, 2920, 2852, 1694, 1601, 1520, 1479, 1403, 1377, 1318, 1120, 1041, 976, 909, 857, 786, 733, 693, 610 cm$^{-1}$; MALDI-FTMS (NBA-NaI) m/z 416.2632 (C$_{25}$H$_{37}$NO$_2$S+H$^+$ requires 416.2618).

1-[5-(3-Furyl)oxazol-2-yl]-1-oxo-9(Z)-octadecene. (159) 5-(3-Furyl)oxazole. This material was prepared from 3-furaldehyde using the procedure described for 5-(thiazol-2-yl)oxazole. Column chromatography (SiO$_2$, 2.5×12 cm, 10% Et$_2$O-hexanes) afforded 5-(3-furyl)oxazole (212 mg, 1.57 mmol, 16%) a yellow oil: $^1$H NMR (CDCl$_3$, 250 MHz) δ 7.85 (s,1H), 7.48 (s,1H), 7.44 (d, 1H, J=1.8 Hz), 7.12 (s, 1H), 6.62 (d, 1H, J=1.8 Hz).

1-[5-(3-Furyl)oxazol-2-yl]-1-oxo-9(Z)octadecene. (159) This material was prepared from 5-(3-furyl)oxazole using the procedure described for 162. Column chromatography (SiO$_2$, 1.5×12 cm, 5% Et$_2$O-hexanes) afforded 159 (54.8 mg, 0.137 mmol, 21%) a pale yellow oil: MALDI-FTMS (NBA-NaI) m/z 400.2848 (C$_{25}$H$_{37}$NO$_3$+H$^+$ requires 400.2846).

1-(4-Phenyloxazol-2-yl)-1-oxo-9(Z)-octadecene. (162) A solution of 4-phenyloxazole (Giardina, et al. *J. Med. Chem.* 1997, 40, 1794-1807) (94.4 mg, 0.65 mmol, 1.0 equiv) in anhydrous THF (5.0 mL) at −78° C. was treated dropwise with a solution of BuLi in hexanes (2.5 M, 0.29 mL, 0.725 mmol, 1.1 equiv) under N$_2$ and the resulting solution was stirred at −78° C. for 20 min. A solution of ZnCl$_2$ in THF (0.5 M, 2.60 mL, 1.30 mmol, 2.0 equiv) was added to the mixture, and the mixture was warmed to 0° C. After stirring at 0° C. for 45 min, CuI (107 mg, 0.56 mmol, 1.0 equiv) was added to the mixture. This was then stirred at 0° C. for 10 min, a solution of 9(Z)-octadecen-1-oyl chloride (prepared from 385 mg of oleic acid and 0.34 mL of oxalyl chloride, 1.30 mmol, 2.0 equiv) in anhydrous THF (3.0 mL) was added dropwise to the mixture, and the mixture was stirred at 0° C. for an additional 1 h. The reaction mixture was diluted with a 1:1 mixture of hexanes and ethyl acetate (60 mL) and washed with 15% NH$_4$OH (2×30 mL), water (30 mL) and saturated aqueous NaCl (30 mL), successively. The organic layer was dried over anhydrous Na$_2$SO$_4$, filtered, and evaporated. Column chromatography (SiO$_2$, 2.5×12 cm, 3% Et$_2$O-hexanes) afforded 162 (115 mg, 0.282 mmol, 43%) as a colorless oil: MALDI-FTMS (NBA-NaI) m/z 432.2886 (C$_{27}$H39NO$_2$+Na$^+$ requires 432.2873).

1-(4(Pyridin-2-yl)oxazol-2-yl)octadec-9-en-1-one. (163) A solution of 2-(oxazol-4-yl)pyridine (4 mg, 0.027 mmol) in anhydrous THF (1 mL) cooled to −75° C. under N$_2$ was treated with n-BuLi (2.5 M in hexanes, 1.1 equiv, 0;030 mmol, 12 mL), and stirred for 20 min. ZnCl$_2$ (0.5 M in THF, 2.0 equiv, 0.054 mmol, 22 mL) was added at −75° C., and stirred for 45 min at 0° C. CuI (1.0 equiv, 0.027 mmol, 5 mg) was added, and the solution was stirred for 10 min at 0° C. A separate flask was charged with oleic acid (2 equiv, 0.054 mmol, 15 mg) in anhydrous CH$_2$Cl$_2$ (0.5 mL), and to this solution cooled to 0° C. under N$_2$ was added oxalyl chloride (5 equiv, 0.27 mmol, 34 mg, 24 mL). After stirring at rt for 2 h, the solution was concentrated under reduced pressure and dissolved in anhydrous THF (0.5 mL). The solution of oleoyl chloride was added and the solution was stirred for 1 h at 0° C. The reaction was diluted with EtOAc (10 mL), and washed with 15% aqueous NH$_4$OH (1×10 mL), H$_2$O (1×10 mL), and saturated aqueous NaCl (1×10 mL). The organic layer was dried (Na$_2$SO$_4$), filtered, and concentrated under reduced pressure. Flash chromatography (SiO$_2$, 1.5 cm×17.5 cm, 2% MeOH—CH$_2$Cl$_2$) afforded 1-(4-(pyridin-2-yl)oxazol-2-yl)octadec-9-en-1-one (163) (5 mg, 0.011 mmol, 42% yield) as a brown residue: $^1$H NMR (CDCl$_3$, 250 MHz) d 8.66 (br d, J=4.8 Hz,1H), 7.90-7.68 (m, 4H), 5.40-5.25 (m, 2H), 3.10 (t, J=7.4 Hz, 2H), 2.10-1.93 (m, 4H), 1.80-1.72 (m, 2H), 1.47-1.17 (m, 20H), 0.86 (br t, J=6.6 Hz, 3H); IR (CDCl$_3$) u$_{max}$ 2925, 2860, 1705, 1605, 1570, 1501, 1425, 1385 cm$^{-1}$; MALDI-FTMS (DHB) m/z 411.3003 (C$_{26}$H$_{38}$N$_2$O$_2$+H$^+$ requires 411.3006).

1-(4(Pyridin-3-yl)oxazol-2-yl)octadec-9-en-1-one. (164) A solution of 3-(oxazol-4-yl)pyridine (6 mg, 0.041 mmol) in anhydrous THF (1 mL) cooled to −75° C. under N$_2$ was treated with n-BuLi (2.5 M in hexanes, 1.1 equiv, 0.045 mmol, 18 mL), and stirred for 20 min. ZnCl$_2$ (0.5 M in THF, 2.0 equiv, 0.082 mmol, 33 mL) was added at −75° C., and stirred for 45 min at 0C. CuI (1.0 equiv, 0.041 mmol, 8 mg) was added, and the solution was stirred for 10 min at 0° C. A separate flask was charged with oleic acid (2 equiv, 0.082 mmol, 23 mg) in anhydrous CH$_2$Cl$_2$ (0.5 mL), and to this solution cooled to 0° C. under N$_2$ was added oxalyl chloride (5 equiv, 0.41 mmol, 52 mg, 37 mL). After stirring at rt for 2 h, the solution was concentrated under reduced pressure and dissolved in anhydrous THF (0.5 mL). The solution of oleoyl chloride was added and the solution was stirred for 1 h at 0° C. The reaction was diluted with EtOAc (10 mL), and washed with 15% aqueous NH$_4$OH (1×10 mL), H$_2$O (1×10 mL), and saturated aqueous NaCl (1×10 mL). The organic layer was dried (Na$_2$SO$_4$), filtered, and concentrated under reduced pressure. Flash chromatography (SiO$_2$, 1.5 cm×17.5 cm, 2% MeOH—CH$_2$Cl$_2$) afforded 1-(4-(pyridin-3-yl)oxazol-2-yl)octadec-9-en-1-one (164) (4 mg, 0.009 mmol, 23% yield) as a brown residue: $^1$H NMR (CDCl$_3$, 250 MHz) d 8.99 (br s, 1H), 8.65 (br d, J=4.7 Hz, 1H), 8.04 (br d, J=7.5 Hz, 1H), 7.86-7.54 (m, 2H), 5.41-5.26 (m, 2H), 3.10 (t, J=7.4 Hz, 2H), 2.10-1.93 (m, 4H), 1.83-1.70 (m, 2H), 1.45-1.20 (m, 20H), 0.86 (br t, J=6.6 Hz, 3H); IR (CDCl$_3$) u$_{max}$ 2926, 2871, 1700, 1601, 1564, 1510, 1421, 1382 cm$^{-1}$; MALDI-FTMS (DHB) m/z 411.3012 (C$_{26}$H$_{38}$N$_2$O$_2$+H$^+$ requires 411.3006).

1-(4-Pyridin-4-yl)oxazol-2-yl)octadec-9-en-1-one. (165) A solution of 4-(oxazol-4-yl)pyridine (3 mg, 0.021 mmol) in anhydrous THF (1 mL) cooled to −75° C. under N$_2$ was treated with n-BuLi (2.5 M in hexanes, 1.1 equiv, 0.023 mmol, 9 mL), and stirred for 20 min. ZnCl$_2$ (0.5 M in THF, 2.0 equiv, 0.042 mmol, 17 mL) was added at −75° C., and stirred for 45 min at 0° C. CuI (1.0 equiv, 0.021 mmol, 4 mg) was added, and the solution was stirred for 10 min at 0° C. A separate flask was charged with oleic acid (2 equiv, 0.042 mmol, 12 mg) in anhydrous CH$_2$Cl$_2$ (0.5 mL), and to this solution cooled to 0° C. under N$_2$ was added oxalyl chloride (5 equiv, 0.21 mmol, 27 mg, 19 mL). After stirring at rt for 2 h, the solution was concentrated under reduced pressure and dissolved in anhydrous THF (0.5 mL). The solution of oleoyl chloride was added and the solution was stirred for 1 h at 0° C. The reaction was diluted with EtOAc (10 mL), and washed with 15% aqueous NH$_4$OH (1×10 mL), H$_2$O (1×10 mL), and saturated aqueous NaCl (1×10 mL). The organic layer was dried (Na$_2$SO$_4$), filtered, and concentrated under reduced pressure. Flash chromatography (SiO$_2$, 1.5 cm×17.5 cm, 2% MeOH—CH$_2$Cl$_2$) afforded 1-(4-(pyridin-4-yl)oxazol-2-yl)octadec-9-en-1-one (165) (2 mg, 0.005 mmol, 24% yield) as a brown residue: $^1$H NMR (CDCl$_3$, 250 MHz) d 8.75 (m, 2H), 7.70-7.61 (m, 3H), 5.42-5.27 (m, 2H), 3.09 (t, J=7.4 Hz, 2H), 2.12-1.89 (m, 4H), 1.82-1.75 (m, 2H), 1.48-1.21 (m, 20H), 0.87 (br t, J=6.8 Hz, 3H); IR (CDCl$_3$) u$_{max}$ 2926, 2873, 1702, 1612, 1559, 1512, 1425, 1380 cm$^{-1}$; MALDI-FTMS (DHB) r/z 411.2997 (C$_{26}$H$_{38}$N$_2$O$_2$+H$^+$ requires 411.3006).

1-(5-(Pyridin-2-yl)oxazol-2-yl)octadecan-1-one. (182) A solution of 2-(oxazol-5-yl)pyridine (113 mg, 0.77 mmol) in anhydrous THF (5 mL) cooled to −75° C. under N$_2$ was treated with n-BuLi (2.5 M in hexanes, 1.1 equiv, 0.85 mmol, 0.34 mL), and stirred for 20 min. ZnCl$_2$ (0.5 M in THF, 2.0 equiv, 1.54 mmol, 3.1 mL) was added at −75° C., and stirred for 45 min at 0° C. CuI (1.0 equiv, 0.77 mmol, 147 mg) was added, and the solution was stirred for 10 min at 0° C. A separate flask was charged with stearic acid (2 equiv, 1.54 mmol, 440 mg) in anhydrous CH$_2$Cl$_2$ (4.2 mL), and to this solution cooled to 0° C. under N$_2$ was added oxalyl chloride (5 equiv, 7.7 mmol, 0.98 g, 0.68 mL). After stirring at rt for 2 h, the solution was concentrated under reduced pressure and dissolved in anhydrous THF (1.5 mL). The solution of stearoyl chloride was added and the solution was stirred for 1 h at 0° C. The reaction was diluted with EtOAc (10 mL), and washed with 15% aqueous NH$_4$OH (1×10 mL), H$_2$O (1×10 mL), and saturated aqueous NaCl (1×10 mL). The organic layer was dried (Na$_2$SO$_4$), filtered, and concentrated under reduced pressure. Flash chromatography (SiO$_2$, 2.5 cm×17.5 cm, 20% EtOAc-hexanes) afforded 1-(5-(pyridin-2-yl)oxazol-2-yl)octadecan-1-one (182) (97 mg, 0.24 mmol, 31% yield) as a white powder: mp 86-87° C.; $^1$H NMR (CDCl$_3$, 250 MHz) d 8.66 (br d, J=5.4 Hz, 1H), 7.89-7.76 (m, 3H), 7.34-7.27 (m, 1H), 3.10 (t, J=7.7 Hz, 2H), 1.82-1.74 (m, 2H), 1.44-1.19 (m, 28H), 0.87 (br t, J=6.6 Hz, 3H); $^{13}$C NMR (CDCl$_3$, 62.5 MHz) d 188.6, 157.4, 153.2, 150.1 (2C), 137.1, 126.8, 124.1, 120.3, 39.2, 31.9, 29.7 (5C), 29.6 (2C), 29.6, 29.4, 29.3 (2C), 29.2, 24.0, 22.7, 14.1; IR (KBr) u$_{max}$ 2942, 2871, 1701, 1601, 1429, 1376 cm$^{-1}$; MALDI-FTMS (DHB) m/z 413.3170 (C$_{26}$H$_{40}$N$_2$O$_2$+H$^+$ requires 713.3162).

1-(5-(Pyridin-2-yl)oxazol-2-yl)hexadecan-1-one. (183) A solution of 2-(oxazol-5-yl)pyridine (95 mg, 0.65 mmol) in anhydrous THF (5 mL) cooled to −75° C. under N$_2$ was treated with n-BuLi (2.5 M in hexanes, 1.1 equiv, 0.72 mmol, 0.29 mL), and stirred for 20 min. ZnCl$_2$ (0.5 M in THF, 2.0 equiv, 1.30 mmol, 2.6 mL) was added at −75° C., and stirred for 45 min at 0° C. CuI (1.0 equiv, 0.65 mmol, 124 mg) was added, and the solution was stirred for 10 min at 0° C. Palmitoyl chloride (2 equiv, 1.3 mmol, 357 mg, 0.39 mL) was added and the solution was stirred for 1 h at 0° C. The reaction was diluted with EtOAc (10 mL), and washed with 15% aqueous NH$_4$OH (1×10 mL), H$_2$O (1×10 mL), and saturated aqueous NaCl (1×10 mL). The organic layer was dried (Na$_2$SO$_4$), filtered, and concentrated under reduced pressure. Flash chromatography (SiO$_2$, 2.5 cm×17.5 cm, 20% EtOAc-hexanes) afforded 1-(5-(pyridin-2-yl)oxazol-2-yl)hexadecan-1-one (183) (103 mg, 0.27 mmol, 42% yield) as an off-white powder: mp 78-80° C.; $^1$H NMR (CDCl$_3$, 250 MHz) d 8.66 (br d, J=5.1 Hz, 1H), 7.88-7.76 (m, 3H), 7.34-7.27 (m, 1H), 3.10 (t, J =7.3 Hz, 2H), 1.83-1.70 (m, 2H), 1.24 (br s, 24H), 0.87 (br t, J=6.9 Hz, 3H); $^{13}$C NMR (CDCl$_3$, 62.5 MHz) d 188.6, 157.4, 153.2, 150.1, 146.3, 137.0, 126.8, 124.1, 120.4, 39.2, 31.9, 29.6 (2C), 29.6 (2C), 29.4 (2C), 29.3 (3C), 29.2 24.0, 22.7, 14.1; IR (KBr) u$_{max}$ 2935, 2847, 1699, 1605, 1425, 1381 cm$^{-1}$; MALDI-FTMS (DHB) m/z 385.2841 (C$_{24}$H$_{36}$N$_2$O$_2$+H$^+$ requires 385.2849).

1-(5-(Pyridin-2-yl)oxazol-2-yl)tetradecan-1-one. (184) A solution of 2-(oxazol-5-yl)pyridine (97 mg, 0.66 mmol) in anhydrous THF (5 mL) cooled to −75° C. under N$_2$ was treated with n-BuLi (2.5 M in hexanes, 1.1 equiv, 0.73 mmol, 0.29 mL), and stirred for 20 min. ZnCl$_2$ (0.5 M in THF, 2.0 equiv, 1.32 mmol, 2.7 mL) was added at −75° C., and stirred for 45 min at 0° C. CuI (1.0 equiv, 0.66 mmol, 126 mg) was added, and the solution was stirred for 10 min at 0° C. A separate flask was charged with myristic acid (2 equiv, 1.32 mmol, 303 mg) in anhydrous CH$_2$Cl$_2$ (4.2 mL), and to this solution cooled to 0° C. under N$_2$ was added oxalyl chloride (5 equiv, 6.6 mmol, 0.84 g, 0.58 mL). After stirring at rt for 2 h, the solution was concentrated under reduced pressure and dissolved in anhydrous THF (1.5 mL). The solution of myristoyl chloride was added and the solution was stirred for 1 h at 0° C. The reaction was diluted with EtOAc (10 mL), and washed with 15% aqueous NH$_4$OH (1×10 mL), H$_2$O (1×10 mL), and saturated aqueous NaCl (1×10 mL). The organic layer was dried (Na$_2$SO$_4$), filtered, and concentrated under reduced pressure. Flash chromatography (SiO$_2$, 2.5 cm×17.5 cm, 20% EtOAc-hexanes) afforded 1-(5-(pyridin-2-yl)oxazol-2-yl)tetradecan-1-one (184) (102 mg, 0.29 mmol, 44% yield) as a white powder: mp 79-80° C.; $^1$H NMR (CDCl$_3$, 250 MHz) d 8.65 (br d, J=4.8 Hz,1H), 7.89-7.75 (m, 3H), 7.34-7.25 (m,1H), 3.10 (t, J =7.3 Hz, 2H), 1.80-1.70 (m, 2H), 1.43-1.18 (m, 20H), 0.86 (br t, J=6.6 Hz, 3H); $^{13}$C NMR (CDCl$_3$, 62.5 MHz) d 188.6, 157.4, 153.2, 150.1 (2C), 146.4, 137.1, 126.8, 124.1, 120.3, 39.1, 31.9, 29.6 (2C), 29.6, 29.4, 29.3 (2C), 29.2, 24.0, 22.7, 14.1; IR (KBr) u$_{max}$ 2960, 2878, 1705, 1598, 1426, 1387 cm$^{31}$ $^1$; MALDI-FTMS (DHB) m/z 357.2536 (C$_{22}$H$_{32}$N$_2$O$_2$+H$^+$ requires 357.2536).

1-(5-(Pyridin-2-yl)oxazol-2-yl)dodecan-1-one. (185) A solution of 2-(oxazol-5-yl)pyridine (102 mg, 0.70 mmol) in anhydrous THF (5 mL) cooled to −75° C. under N$_2$ was treated with n-BuLi (2.5 M in hexanes, 1.1 equiv, 0.77 mmol, 0.31 mL), and stirred for 20 min. ZnCl$_2$ (0.5 M in THF, 2.0 equiv, 1.40 mmol, 2.8 mL) was added at −75° C., and stirred for 45 min at 0° C. CuI (1.0 equiv, 0.70 mmol, 133 mg) was added, and the solution was stirred for 10 min at 0° C. Lauroyl chloride (2 equiv, 1.4 mmol, 306 mg, 0.32 mL) was added and the solution was stirred for 1 h at 0° C. The reaction was diluted with EtOAc (10 mL), and washed with 15% aqueous NH$_4$OH (1×10 mL), H$_2$O (1×10 mL), and saturated aqueous NaCl (1×10 mL). The organic layer was dried (Na$_2$SO$_4$), filtered, and concentrated under reduced pressure. Flash chromatography (SiO$_2$, 2.5 cm×17.5 cm, 20% EtOAc-hexanes) afforded 1-(5-(pyridin-2-yl)oxazol-2-yl)dodecan-1-one (185) (122 mg, 0.37 mmol, 53% yield) as an off-white powder: mp 73-74° C.; $^1$H NMR (CDCl$_3$, 250 MHz) d 8.65 (br d, J=4.0 Hz, 1H), 7.89-7.75 (m, 3H), 7.34-7.25 (m, 1H), 3.09 (t, J =7.7 Hz, 2H), 1.83-1.69 (m, 2H), 1.41-1.19 (m, 16H), 0.86 (br t, J=7.0 Hz, 3H); $^{13}$C NMR (CDCl$_3$, 62.5 MHz) d 188.6, 153.2, 150.1 (2C), 146.3, 137.1, 126.8, 124.1, 120.3, 39.1, 31.9, 29.6 (2C), 29.4, 29.3, 29.2 (2C), 24.0, 22.7, 14.1; IR (KBr) u$_{max}$ 2929, 2857, 1704, 1609, 1415, 1378 cm$^{-1}$; MALDI-FTMS (DHB) m/z 329.2214 (C$_{20}$H$_{28}$N$_2$O$_2$+H$^+$ requires 329.2223).

1-(5-(Pyridin-2-yl)oxazol-2-yl)decan-1-one. (187) A solution of 2-(oxazol-5-yl)pyridine (100 mg, 0.68 mmol) in anhydrous THF (5 mL) cooled to −75° C. under N$_2$ was treated with n-BuLi (2.5 M in hexanes, 1.1 equiv, 0.75 mmol, 0.30 mL), and stirred for 20 min. ZnCl$_2$ (0.5 M in THF, 2.0 equiv, 1.40 mmol, 2.8 mL) was added at −75° C., and stirred for 45 min at 0° C. CuI (1.0 equiv, 0.68 mmol, 130 mg) was added, and the solution was stirred for 10 min at 0° C. Decanoyl chloride (2 equiv, 1.4 mmol, 270 mg, 0.29 mL) was added and the solution was stirred for 1 h at 0° C. The reaction was diluted with EtOAc (10 mL), and washed with 15% aqueous NH$_4$OH (1×10 mL), H$_2$O (1×10 mL), and saturated aqueous NaCl (1×10 mL). The organic layer was dried (Na$_2$SO$_4$), filtered, and concentrated under reduced pressure. Flash chromatography (SiO$_2$, 2.5 cm×17.5 cm, 20% EtOAc-hexanes) afforded 1-(5-(pyridin-2-yl)oxazol-2-yl)decan-1-one (187) (80 mg, 0.27 mmol, 40% yield) as a light brown powder: mp 56-57° C.; $^1$H NMR (CDCl$_3$, 250 MHz) d 8.69-8.62 (m, 1H), 7.87-7.75 (m, 3H), 7.33-7.25 (m, 1H), 3.08 (t, J=7.7 Hz, 2H), 1.81-1.69 (m, 2H), 1.41-1.19 (m, 12H), 0.86 (br t, J=7.0 Hz, 3H); $^{13}$C NMR (CDCl$_3$, 62.5 MHz) d 188.5, 157.3, 153.1, 150.0, 146.2, 136.9, 127.8, 124.1, 120.3, 39.1, 31.8, 29.4, 29.3, 29.2, 29.1, 24.0, 22.6, 14.0; IR (KBr) u$_{max}$ 2930, 2845, 1697, 1601, 1422, 1380 cm$^{-1}$; MALDI-FTMS (DHB) m/z300.1911 (C$_{18}$H$_{24}$N$_2$O$_2$+H$^+$ requires 301.1910).

1-(5-(Pyridin-2-yl)oxazol-2-yl)nonan-1-one. (188) A solution of 2-(oxazol-5-yl)pyridine (117 mg, 0.80 mmol) in anhydrous THF (5 mL) cooled to −75° C. under N$_2$ was treated with n-BuLi (2.5 M in hexanes, 1.1 equiv, 0.88 mmol, 0.35 mL), and stirred for 20 min. ZnCl$_2$ (0.5 M in THF, 2.0 equiv, 1.60 mmol, 3.2 mL) was added at −75° C., and stirred for 45 min at 0° C. CuI (1.0 equiv, 0.80 mmol, 152 mg) was added, and the solution was stirred for 10 min at 0° C. A separate flask was charged with nonanoic acid (2 equiv, 1.60 mmol, 253 mg, 0.28 mL) in anhydrous CH$_2$Cl$_2$ (4.2 mL), and to this solution cooled to 0° C. under N$_2$ was added oxalyl chloride (5 equiv, 8.0 mmol, 1.02 g, 0.70 mL). After stirring at rt for 2 h, the solution was concentrated under reduced pressure and dissolved in anhydrous THF (1.5 mL). The solution of nonanoyl chloride was added and the solution was stirred for 1 h at 0° C. The reaction was diluted with EtOAc (10 mL), and washed with 15% aqueous NH$_4$OH (1×10 mL), H$_2$O (1×10 mL), and saturated aqueous NaCl (1×10 mL). The organic layer was dried (Na$_2$SO$_4$), filtered, and concentrated under reduced pressure. Flash chromatography (SiO$_2$, 2.5 cm×17.5 cm, 20% EtOAc-hexanes) afforded 1-(5-(pyridin-2-yl)oxazol-2-yl)nonan-1-one (188) (94 mg, 0.33 mmol, 41% yield) as a light brown powder: mp 56-57° C.; $^1$H NMR (CDCl$_3$, 250 MHz) d 8.61 (br d, J=4.4 Hz, 1H), 7.84-7.71 (m, 3H), 7.29-7.22 (m, 1H), 3.05 (t, J=7.3 Hz, 2H), 1.79-1.66 (m, 2H), 1.42-1.16 (m, 10H), 0.88-0.77 (m, 3H); $^{13}$C NMR (CDCl$_3$, 62.5 MHz) d 188.4, 157.3, 153.1, 150.0, 146.2, 137.0, 126.8, 124.0, 120.3, 39.0, 31.7, 29.2, 29.0, 24.0, 23.9, 22.5, 14.0; IR (KBr) u$_{max}$ 2922, 2856, 1705, 1697, 1600, 1420, 1381 cm$^{-1}$; MALDI-FTMS (DHB) m/z 287.1744 (C$_{17}$H$_{22}$N$_2$O$_2$+H$^+$ requires 287.1754).

1-(5-(Pyridin-2-yl)oxazol-2-yl)octan-1-one. (189) A solution of 2-(oxazol-5-yl)pyridine (111 mg, 0.76 mmol) in anhydrous THF (5 mL) cooled to −75° C. under N$_2$ was treated with n-BuLi (2.5 M in hexanes, 1.1 equiv, 0.84 mmol, 0.33 mL), and stirred for 20 min. ZnCl$_2$ (0.5 M in THF, 2.0 equiv, 1.52 mmol, 3.0 mL) was added at −75° C., and stirred for 45 min at 0° C. CuI (1.0 equiv, 0.76 mmol, 145 mg) was added, and the solution was stirred for 10 min at 0° C. A separate flask was charged with octanoic acid (2 equiv, 1.52 mmol, 219 mg, 0.24 mL) in anhydrous $CH_2Cl_2$ (4.2 mL), and to this solution cooled to 0° C. under $N_2$ was added oxalyl chloride (5 equiv, 7.6 mmol, 0.96 g, 0.66 mL). After stirring at rt for 2 h, the solution was concentrated under reduced pressure and dissolved in anhydrous THF (1.5 mL). The solution of octanoyl chloride was added and the solution was stirred for 1 h at 0° C. The reaction was diluted with EtOAc (10 mL), and washed with 15% aqueous $NH_4OH$ (1×10 mL), $H_2O$ (1×10 mL), and saturated aqueous NaCl (1×10 mL). The organic layer was dried ($Na_2SO_4$), filtered, and concentrated under reduced pressure. Flash chromatography ($SiO_2$, 2.5 cm×17.5 cm, 20% EtOAc-hexanes) afforded 1-(5-(pyridin-2-yl)oxazol-2-yl)octan-1-one (189) (107 mg, 0.39 mmol, 52% yield) as a light brown powder: mp 56° C; $^1H$ NMR ($CDCl_3$, 250 MHz) d 8.63 (br d, J=4.8 Hz, 1H), 7.85-7.74 (m, 3H), 7.28 (br t, J=5.1 Hz, 1H), 3.08 (t, J=7.3 Hz, 2H), 1.84-1.67 (m, 2H), 1.47-1.17 (m, 8H), 0.85 (br t, J=6.6 Hz, 3H); $^{13}C$ NMR ($CDCl_3$, 62.5 MHz) d 188.5, 157.3, 153.1, 150.0, 146.2, 137.0, 127.8, 124.1, 120.3, 39.1, 31.6, 29.0, 28.9, 24.0, 22.5, 14.0; IR (KBr) $u_{max}$ 2926, 2849, 1694, 1601, 1499, 1470, 1426, 1382 $cm^{-1}$; MALDI-FTMS (DHB) m/z 273.1595 ($C_{16}H_{20}N_2O_2+H^+$ requires 273.1597).

1-(5-(Pyridin-2-yl)oxazol-2-yl)heptan-1-one. (190) A solution of 2-(oxazol-5-yl)pyridine (112 mg, 0.77 mmol) in anhydrous THF (5 mL) cooled to −75° C. under $N_2$ was treated with n-BuLi (2.5 M in hexanes, 1.1 equiv, 0.85 mmol, 0.34 mL), and stirred for 20 min. $ZnCl_2$ (0.5 M in THF, 2.0 equiv, 1.58 mmol, 3.1 mL) was added at −75° C., and stirred for 45 min at 0° C. CuI (1.0 equiv, 0.77 mmol, 146 mg) was added, and the solution was stirred for 10 min at 0° C. A separate flask was charged with heptanoic acid (2 equiv, 1.55 mmol, 202 mg, 0.22 mL) in anhydrous $CH_2Cl_2$ (4.2 mL), and to this solution cooled to 0° C. under $N_2$ was added oxalyl chloride (5 equiv, 7.8 mmol, 0.99 g, 0.68 mL). After stirring at rt for 2 h, the solution was concentrated under reduced pressure and dissolved in anhydrous THF (1.5 mL). The solution of heptanoyl chloride was added and the solution was stirred for 1 h at 0° C. The reaction was diluted with EtOAc (10 mL), and washed with 15% aqueous $NH_4OH$ (1×10 mL), $H_2O$ (1×10 mL), and saturated aqueous NaCl (1×10 mL). The organic layer was dried ($Na_2SO_4$), filtered, and concentrated under reduced pressure. Flash chromatography ($SiO_2$, 2.5 cm×17.5 cm, 20% EtOAc-hexanes) afforded 1-(5-(pyridin-2-yl)oxazol-2-yl)heptan-1-one (190) (97 mg, 0.38 mmol, 49% yield) as a light brown powder mp 52° C.; $^1H$ NMR ($CDCl_3$, 250 MHz) d 8.63 (br d, J=4.8 Hz, 1H), 7.85-7.74 (m, 3H), 7.31-7.25 (m, 1H), 3.08 (t, J=7.7 Hz, 2H), 1.78-1.69 (m, 2H), 1.44-1.22 (m, 6H), 0.68 (t, J=6.6 Hz, 3H); 13C NMR ($CDCl_3$, 62.5 MHz) d 188.5, 157.3, 153.2, 150.0, 146.3, 137.0, 126.8, 124.1, 120.3, 39.1, 31.4, 28.8, 23.9, 22.4, 14.0; IR (KBr) $u_{max}$ 2933, 2847, 1698, 1604, 1430, 1387 $cm^{-1}$; MALDI-FTMS (DHB) m/z 259.1436 ($C_{15}H_{18}N_2O_2+H^+$ requires 259.1441).

1-(5-(Pyridin-2-yl)oxazol-2-yl)hexan-1-one. (191) A solution of 2-(oxazol-5-yl)pyridine (116 mg, 0.79 mmol) in anhydrous THF (5 mL) cooled to −75° C. under $N_2$ was treated with n-BuLi (2.5 M in hexanes, 1.1 equiv, 0.87 mmol, 0.35 mL), and stirred for 20 min. $ZnCl_2$ (0.5 M in THF, 2.0 equiv, 1.58 mmol, 3.2 mL) was added at −75° C., and stirred for 45 min at 0° C. CuI (1.0 equiv, 0.79 mmol, 151 mg) was added, and the solution was stirred for 10 min at 0° C. A separate flask was charged with hexanoic acid (2 equiv, 1.58 mmol, 186 mg, 0.20 mL) in anhydrous $CH_2Cl_2$ (4.2 mL), and to this solution cooled to 0° C. under $N_2$ was added oxalyl chloride (5 equiv, 8.0 mmol, 1.02 g, 0.70 mL). After stirring at rt for 2 h, the solution was concentrated under reduced pressure and dissolved in anhydrous THF (1.5 mL). The solution of hexanoyl chloride was added and the solution was stirred for 1 h at 0° C. The reaction was diluted with EtOAc (10 mL), and washed with 15% aqueous $NH_4OH$ (1×10 mL), $H_2O$ (1×10 mL), and saturated aqueous NaCl (1×10 mL). The organic layer was dried ($Na_2SO_4$), filtered, and concentrated under reduced pressure. Flash chromatography ($SiO_2$, 2.5 cm×17.5 cm, 20% EtOAc-hexanes) afforded 1-(5-(pyridin-2-yl)oxazol-2-yl)hexan-1-one (191) (50 mg, 0.20 mmol, 25% yield) as a light brown powder: mp 49-50.5° C.; $^1H$ NMR ($CDCl_3$, 250 MHz) d 8.64 (br d, J=3.9 Hz, 1H), 7.85-7.75 (m, 3H), 7.32-7.26 (m, 1H), 3.09 (t, J=7.7 Hz, 2H), 1.82-1.70 (m, 2H), 1.40-1.31 (m, 4H), 0.89 (t, J=6.95 Hz, 3H); 13C NMR ($CDCl_3$, 62.5 MHz) d 181.5, 150.3, 146.2, 143.0, 139.3, 130.0, 119.8, 117.0, 113.3, 32.0, 24.2, 16.5, 15.3, 6.8; IR (KBr) $u_{max}$ 2957, 2872, 1700, 1677, 1603, 1426, 1387 $cm^{-1}$; MALDI-FTMS (DHB) m/z 245.1284 ($C_{14}H_{16}N_2O_2+H^+$ requires 245.1284).

1 (5-(Pyridin-2-yl)oxazol-2-yl)pentan-1-one. (192) A solution of 2-(oxazol-5-yl)pyridine (116 mg, 0.79 mmol) in anhydrous THF (5 mL) cooled to −75° C. under $N_2$ was treated with n-BuLi (2.5 M in hexanes, 1.1 equiv, 0.87 mmol, 0.35 mL), and stirred for 20 min. $ZnCl_2$ (0.5 M in THF, 2.0 equiv, 1.58 mmol, 3.2 mL) was added at −75° C., and stirred for 45 min at 0° C. CuI (1.0 equiv, 0.79 mmol, 151 mg) was added, and the solution was stirred for 10 min at 0° C. A separate flask was charged with valeric acid (2 equiv, 1.58 mmol, 161 mg, 0.17 mL) in anhydrous $CH_2Cl_2$ (4.2 mL), and to this solution cooled to 0° C. under $N_2$ was added oxalyl chloride (5 equiv, 7.89 mmol, 1.00 g, 0.69 mL). After stirring at rt for 2 h, the solution was concentrated under reduced pressure and dissolved in anhydrous THF (1.5 mL). The solution of valeryl chloride was added and the solution was stirred for 1 h at 0° C. The reaction was diluted with EtOAc (10 mL), and washed with 15% aqueous $NH_4OH$ (1×10 mL), $H_2O$ (1×10 mL), and saturated aqueous NaCl (1×10 mL). The organic layer was dried ($Na_2SO_4$), filtered, and concentrated under reduced pressure. Flash chromatography ($SiO_2$, 2.5 cm×17.5 cm, 20% EtOAc-hexanes) afforded 1-(5-(pyridin-2-yl)oxazol-2-yl)pentan-1-one (192) (43 mg, 0.19 mmol, 24% yield) as a light brown powder mp 36-37° C.; $^1H$ NMR ($CDCl_3$, 250 MHz) d 8.68-8.66 (m, 1H), 7.89-7.81 (m, 3H), 7.34-7.29 (m, 1H), 3.12 (t, J=7.7 Hz, 2H), 1.83-1.71 (m, 2H), 1.48-1.39 (m, 2H), 0.96 (t, J=7.3 Hz, 3H); $^{13}C$ NMR ($CDCl_3$, 62.5 MHz) d 188.5, 162.1, 157.6, 150.0, 137.1, 127.9, 126.8, 124.1, 120.3, 38.9, 26.0, 22.2, 13.8; IR (KBr) u. 2954, 2926, 2862, 1700, 1690, 1602, 1472, 1427, 1381, $cm^{-1}$; MALDI-FTMS (DHB) m/z 253.0950 ($C_{13}H_{14}N_2O_2+Na^+$ requires 253.0947).

1-[5-(Pyridin-2-yl)oxazol-2-yl]butan-1-one. (193) A solution of 2-(oxazol-5-yl)pyridine (98 mg, 0.67 mmol) in anhydrous THF (5 mL) cooled to −75° C. under $N_2$ was treated with n-BuLi (2.5 M in hexanes, 1.1 equiv, 0.74 mmol, 0.3 mL), and stirred for 20 min. $ZnCl_2$ (0.5 M in THF, 2.0 equiv, 1.34 mmol, 2.7 mL) was added at −75° C., and stirred for 45 min at 0° C. CuI (1.0 equiv, 0.67 mmol, 128 mg) was added, and the solution was stirred for 10 min at 0° C. Butyryl chloride (2.0 equiv, 1.34 mmol, 143 mg, 0.14 mL) was added and the solution was stirred for 1 h at 0° C. The reaction was diluted with EtOAc (10 mL), and washed with 15% aqueous $NH_4OH$ (1×10 mL), $H_2O$ (1×10 mL), and saturated aqueous NaCl (1×10 mL). The organic layer was dried ($Na_2SO_4$), filtered, and concentrated under reduced pressure. Flash chromatography ($SiO_2$, 2.5 cm×17.5 cm, 20% EtOAc-hexanes) afforded 1-(5-(pyridin-2-yl)oxazol-2-yl)butan-1-one (193) (68 mg, 0.31 mmol, 46% yield) as a light brown powder: mp 54-55° C; $^1H$ NMR ($CDCl_3$, 250 MHz) d 8.65-8.62 (m, 1H), 7.85-7.78 (m, 3H), 7.31-7.26 (m, 1H), 3.07 (t, J=7.3 Hz, 2H), 1.87-1.72 (m, 2H), 1.00 (t, J=7.7 Hz, 3H); $^{13}$C NMR (CDCl$_3$, 62.5 MHz)d 188.4, 162.0, 157.3, 150.1, 146.3, 136.9, 126.8, 124.1, 120.3, 40.9, 17.5, 13.5; IR (KBr) u$_{max}$ 2963, 2933, 2872, 1675, 1469, 1426, 1387, 1227 cm$^{-1}$; MALDI-FTMS (DHB) m/z 217.0968 (C$_{12}$H$_{12}$N$_2$O$_2$+H$^+$ requires 217.0971).

1-[5-(Pyridin-2-yl)oxazol-2-yl]propan-1-one. (194) A solution of 2-(oxazol-5-yl)pyridine (98 mg, 0.67 mmol) in anhydrous THF (5 mL) cooled to −75° C. under N$_2$ was treated with n-BuLi (2.5 M in hexanes, 1.1 equiv, 0.74 mmol, 0.3 mL), and stirred for 20 min. ZnCl$_2$ (0.5 M in THF, 2.0 equiv, 1.34 mmol, 2.7 mL) was added at −75° C., and stirred for 45 min at 0° C. CuI (1.0 equiv, 0.67 mmol, 128 mg) was added, and the solution was stirred for 10 min at 0° C. Propionyl chloride (2.0 equiv, 1.34 mmol, 124 mg, 0.12 mL) was added and the solution was stirred for 1 h at 0° C. The reaction was diluted with EtOAc (10 mL), and washed with 15% aqueous NH$_4$OH (1×10 mL), H$_2$O (1×10 mL), and saturated aqueous NaCl (1×10 mL). The organic layer was dried (Na$_2$SO$_4$), filtered, and concentrated under reduced pressure. Flash chromatography (SiO$_2$, 2.5 cm×17.5 cm, 20% EtOAc-hexanes) afforded 1-[5-(pyridin-2-yl)oxazol-2-yl]propan-1-one (194) (89 mg, 0.44 mmol, 65% yield) as a light brown powder: mp 65-67° C.; $^1$H NMR (CDCl$_3$, 250 MHz) d 8.65-8.62 (m, 1H), 7.86-7.75 (m, 3H), 7.31-7.26 (m, 1H), 3.18-3.08 (m, 2H), 1.29-1.21 (m, 3H); $^{13}$C NMR (CDCl$_3$, 62.5 MHz) d 188.8, 161.9, 157.2, 150.1, 146.3, 136.9, 126.8, 124.0, 120.3, 32.5, 7.8; IR (KBr) u. 2935, 2862, 1699, 1471, 1426, 1377 cm$^{-1}$; MALDI-FTMS (DHB) m/z 203.0818 (C$_{11}$H$_{10}$N$_2$O$_2$+H$^+$ requires 203.0815).

1-Oxo-1-[5-(2-pyridyl)oxazol-2-yl]-2-phenylethane. (195) This material was prepared from 5-(2-pyridyl)oxazole and phenylacetic acid using the procedure described for 162. Column chromatography (SiO$_2$, 1.5×12 cm, 20% EtOAc-hexanes) afforded 195 (5.7 mg, 0.022 mmol, 3%) as a yellow oil: MALDI-FTMS (NBA-NaI) m/z 265.0963 (C$_{16}$H$_{12}$N$_2$O$_2$+H$^+$ requires 265.0971).

1-Oxo-1-[5-(2-pyridyl)oxazol-2-yl]4-phenylpropane. (196) This material was prepared from 5-(2-pyridyl)oxazole and hydrocinnamic acid using the procedure described for 162. Column chromatography (SiO$_2$, 1.5×12 cm, 20% EtOAc-hexanes) afforded 196 (46.9 mg, 0.169 mmol, 26%) a yellow crystalline powder: mp 67.0-70.0° C.; MALDI-FTMS (NBA-NaI) m/z 279.1120 (C$_{17}$H$_{14}$N$_2$O$_2$+H$^+$ requires 279.1128).

1-Oxo-1-[5-(2-pyridyl)oxazol-2-yl].4-phenylbutane. (197) This material was prepared from 5-(2-pyridyl)oxazole and 4-phenylbutyric acid using the procedure described for 162. Column chromatography (SiO$_2$, 1.5×12 cm, 20% EtOAc-hexanes) afforded 197 (28.3 mg, 0.097 mmol, 15%) a yellow crystalline powder: mp 69.0-72.0° C.; MALDI-FTMS (NBA-NaI) m/z 293.1287 (C$_{18}$H$_{16}$N$_2$O$_2$+H$^+$ requires 293.1284).

1-Oxo-1-[5-(2-pyridyl)oxazol-2-yl]-5-phenylpentane. (198) This material was prepared from 5-(2-pyridyl)oxazole and 5phenylpentanoic acid using the procedure described for 162. Column chromatography (SiO$_2$, 1.5×12 cm, 20% EtOAc-hexanes) afforded 198 (39.5 mg, 0.129 mmol, 20%) a yellow crystalline powder: mp 49.0-51.0° C.; MALDI-FTMS (NBA-NaI) m/z 307.1440 (C$_{19}$H$_{18}$N$_2$O$_2$+H$^+$ requires 307.1441).

1-Oxo-1-[5-(2-pyridyl)oxazol-2-yl]-6-phenylhexane. (199) This material was prepared from 5-(2-pyridyl)oxazole and 6-phenylhexanoic acid using the procedure described for 162. Column chromatography (SiO$_2$, 1.5×12 cm, 20% EtOAc-hexanes) afforded 199 (50.0 mg, 0.156 mmol, 24%) a pale yellow crystalline powder: mp 43.5-45.5° C.; MALDI-FTMS (NBA-NaI) m/z 321.1607 (C$_{20}$H$_{20}$N$_2$O$_2$+H$^+$ requires 321.1597).

1-Oxo-1-[5-(2-pyridyl)oxazol-2-yl]-7-phenylheptane. (200) This material was prepared from 5-(2-pyridyl)oxazole and 7-phenylheptanoic acid using the procedure described for 162. Column chromatography (SiO$_2$, 1.5×12 cm, 20% EtOAc-hexanes) afforded 200 (70.9 mg, 0.212 mmol, 33%) a pale yellow crystalline powder: mp 45.0-48.0° C.; MALDI-FTMS (NBA-NaI) m/z 335.1756 (C$_{21}$H$_{22}$N$_2$O$_2$+H$^+$ requires 335.1754).

1-Oxo-1-[5-(2-pyridyl)oxazol-2-yl]-8-phenyloctane. (201) This material was prepared from 5-(2-pyridyl)oxazole and 8-phenyloctanoic acid using the procedure described for 162. Column chromatography (SiO$_2$, 1.5×12 cm, 20% EtOAc-hexanes) afforded 201 (62.6 mg, 0.180 mmol, 28%) a pale yellow crystalline powder mp 72.0-73.0° C.; MALDI-FTMS (NBA-NaI) ml/z 349.1905 (C$_{22}$H$_{24}$N$_2$O$_2$+H$^+$ requires 349.1910).

1-Oxo-1-[5-(2-pyridyl)oxazol-2-yl]-9-phenylnonane. (202) This material was prepared from 5-(2-pyridyl)oxazole and 9-phenylnonanoic acid (Kiuchi, F.; et al. *Chem. Pharm. Bull.* 1997, 45, 685-696) using the procedure described for 162. Column chromatography (SiO$_2$, 1.5×12 cm, 20% EtOAc-hexanes) afforded 202 (88.9 mg, 0.245 mmol, 35%) a pale yellow crystalline powder: mp 39.0-41.0° C.; MALDI-FTMS (NBA-NaI) m/z 363.2058 (C$_{23}$H$_{26}$N$_2$O$_2$+H$^+$ requires 363.2067).

1-Oxo-1-[5-(2-pyridyl)oxazol-2-yl]-9-decene. (203) This material was prepared from 5-(2-pyridyl)oxazole and 9-decenoic acid using the procedure described for 162. Column chromatography (SiO$_{21}$, 1.5×12 cm, 20% EtOAc-hexanes) afforded 203 (64.5 mg, 0.216 mmol, 33%) a pale yellow crystalline powder: mp 55.0-57.0° C.; MALDI-FTMS (NBA-NaI) m/z 299.1748 (C$_{18}$H$_{22}$N$_2$O$_2$+H$^+$ requires 299.1754).

1-Oxo-1-[5-(2-pyridyl)oxazol-2-yl]-9-decyne. (204) This material was prepared from 5-(2-pyridyl)oxazole and 9-decynoic acid using the procedure described for 162. Column chromatography (SiO$_2$, 1.5×12 cm, 20% EtOAc-hexanes) afforded 204 (67.9 mg, 0.229 mmol, 47%) a colorless crystalline powder mp 64.5-65.5° C.; MALDI-FTMS (NBA-NaI) m/z 297.1589 (C$_{18}$H$_{20}$N$_2$O$_2$+H$^+$ requires 297.1597).

1-Oxo-1-[5-(2-pyridyl)oxazol-2-yl]-9-octadecyne. (205) This material was prepared from 5-(2-pyridyl)oxazole and stearolic acid using the procedure described for 162. Column chromatography (SiO$_2$, 1.5×12 cm,20% EtOAc-hexanes) afforded 205 (75.7 mg, 0.185 mmol, 29%) a colorless crystalline powder mp 41.0° C.; MALDI-FTMS (NBA-NaI) m/z 409.2850 (C$_{26}$H$_{36}$N$_2$O$_2$+H$^+$ requires 409.2849).

1-(4,5-Diphenyloxazol-2-yl)-1-oxo-9(Z)-octadecene. (212) 4,5-Diphenyloxazole. A mixture of α-bromo-α-phenylacetophenone (densyl bromide, 5.53 g, 20.10 mmol, 1.0 equiv), ammonium formate (4.4 g, 69.8 mmol, 3.5 equiv) and formic acid (96%, 21.3 mL) were warmed at reflux for 2.5 h. The mixture was cooled to room temperature, added dropwise to ice-cooled water (70 mL), and then the solution was made basic with the addition of 30% aqueous NaOH. It was extracted with ether (200 mL then 100 mL), and the separated organic layer was dried over anhydrous Na$_2$SO$_4$, filtered, and evaporated. Chromatography (SiO$_2$, 2.5×12 cm, 2% EtOAc-hexanes) afforded 4,5-diphenyloxazole (752 mg, 3.40 mmol, 17%) as a pale yellow oil: $^1$H NMR (CDCl$_3$, 250 MHz) δ 7.96 (s, 1H), 7.72-7.59 (m, 4H), 7.45-7.33 (m, 6H).

1-(4,5-Diphenyloxazol-2-yl)-1-oxo-9(Z)-octadecene. This material was prepared from 4,5-diphenyloxazole using the procedure described for 162. Column chromatography (SiO$_2$, 2.5×12 cm, 2% Et$_2$O-hexanes) afforded 212 (33.3 mg, 0.069 mmol, 11%) as a yellow oil: MALDI-FTMS (NBA-NaI) m/z 508.3177 (C$_{33}$H$_{43}$NO$_2$+Na$^+$ requires 508.3186).

1-(4,5-Dimethyloxazol-2-yl)-1-oxo-9(Z)-octadecene. (213)

4,5-Dimethyloxazole. (Theilig, G. *Chem. Ber.* 1953, 86, 96-109) A mixture of 3-chloro-2-butanone (2.50 g, 23.46 mmol, 1.0 equiv), tetrabutylammonium bromide (152 mg, 0.47 mmol, 0.02 equiv) and formamide (7.5 mL) were heated at 100° C. for 6 h. The product was distilled from the mixture under atmospheric pressure to afford 4,5-dimethyloxazole (bath temp. 150-170° C., 796 mg, 8.20 mmol, 35%) as a colorless oil: $^1$H NMR (CDCl$_3$, 250 MHz) δ7.66 (s, 1H), 2.23 (s, 3H), 2.09 (s, 3H).

1-(4,5-Dimethyloxazol-2-yl)- -oxo-9(Z)-octadecene. This material was prepared from 4,5-dimethyloxazole using the procedure described for 162. Column chromatography (SiO$_2$, 2.5×12 cm, 5% Et$_2$O-hexanes) afforded 213 (106 Column chromatography (SiO$_2$, 2.5×12 cm, 5% Et$_2$O-hexanes) afforded 213 (106 mg, 0.293 mmol, 45%) as a pale yellow oil: MALDI-FTMS (NBA-NaI) m/z 362.3049 (C$_{23}$H$_{39}$NO$_2$+H$^+$ requires 362.3054).

1-Hydroxy-1-[5-(2-pyridyl)oxazol-2-yl]-9(Z)-octadecene. Sodium borohydride (1.8 mg, 0.048 mmol) was added to a solution of 1-oxo-1-[5-(2-pyridyl)oxazol-2-yl]-9 (Z)-octadecene (143) (13.0 mg, 0.032 mmol) in a 1:1 mixture of methanol and THF (3.0 mL) at 0° C. After stirring at 0° C. for 20 min, saturated aqueous NaCl was added to the mixture, and the mixture was extracted with ethyl acetate (40 mL). The separated organic layer was dried over anhydrous Na$_2$SO$_4$, filtered, and evaporated. Chromatography (SiO$_2$, 1.5×12 cm, 50% EtOAc-hexanes) afforded 26 (7.2 mg, 0.017 mmol, 55%) as a colorless solid: mp. 37.5-39.5° C.; MALDI-FTMS (NBA-NaI) m/z 413.3164 (C$_{26}$H$_{40}$N$_2$O$_2$+H$^+$ requires 413.3162).

1-[5-(2-Pyridyl)oxazol-2-yl]-9(Z)-octadecene. Triphenylphosphine (69.3 mg, 0.264 mmol, 5.0 equiv) and carbon tetrabromide (87.6 mg, 0.264 mmol, 5.0 equiv) were added to a solution of 1-hydroxy-1-[5-(2-pyridyl)oxazol-2-yl]-9 (Z) -octadecene (26, 21.8 mg, 0.053 mmol) in dichloromethane (2.0 mL) at 0° C. (A similar reaction was reported: Bohlmann, F.; et al. *Chem. Ber.* 1976, 109, 1586-1588). After stirring at 0° C. for 30 min, the mixture was diluted with dichloromethane (50 mL) and washed with water (25 mL). The separated organic layer was dried over anhydrous Na$_2$SO$_4$, filtered, and evaporated. Chromatography (SiO$_2$, 1.5×12 cm, 20% EtOAc-hexanes) afforded 27 (2.1 mg, 0.0053 mmol, 10%) as a pale yellow oil: MALDI-FTMS (NBA-NaI) m/z 397.3209 (C$_{26}$H$_{40}$N$_2$O +H$^+$ requires 397.3213).

What is claimed is:

1. An inhibitor of fatty acid amide hydrolase represented by the following formula:

A-B—C wherein A is an inhibition subunit in the form of an α-keto heterocyclic pharmacophore for inhibiting the fatty acid amide hydrolase, B is a linkage subunit, and C is a binding subunit wherein A-B—C is represented by the formula:

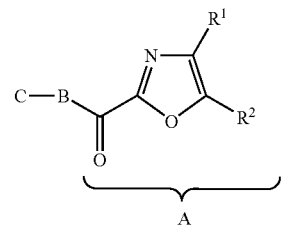

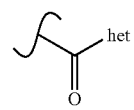

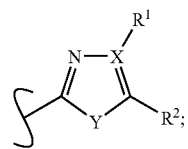

wherein

R$^1$ and R$^2$ are radicals independently selected from the group consisting of hydrogen, C1-C6 alkyl, aromatic ring, and heteroaromatic ring;

with the proviso that R$^1$ and R$^2$ cannot both be hydrogen;

the linkage subunit B is a linear chain of 3 to 9 carbon atoms for linking the inhibition subunit A and the binding subunit C and for enabling the binding subunit C to bind to the binding region on the fatty acid amide hydrolase, the linear skeleton having a first end and a second end, the first end being covalently bonded to the α-keto group of A, wherein the first end of B is an α-carbon with respect to the α-keto group of the inhibition subunit A, and then the α-carbon is optionally mono- or bis-functionalized with substituents selected from the group consisting of fluoro, chloro, hydroxyl, alkoxy, trifluoromethyl, and alkyl; and the binding subunit C is a π-bond containing radical having a π-unsaturation and being selected from a group consisting of aryl, alkynyl, and ring structures having at least one unsaturation, with or without one or more heteroatoms, the binding subunit C being covalently bonded to the second end of the linkage subunit B, the π-unsaturation within the π-bond containing radical being separated from the α-keto group of A by a sequence of no less than 3 and no more than 9 atoms bonded sequentially to one another, inclusive of the linear skeleton for enabling the π-unsaturation to bind to the binding region of the fatty acid amide hydrolase while the inhibition subunit A inhibits the fatty acid amide hydrolase.

2. An inhibitor of fatty acid amide hydrolase according to claim 1 wherein $R^1$ and $R^2$ are radicals independently selected from the group consisting of hydrogen, C1-C6 alkyl, and radicals represented by the following structures:

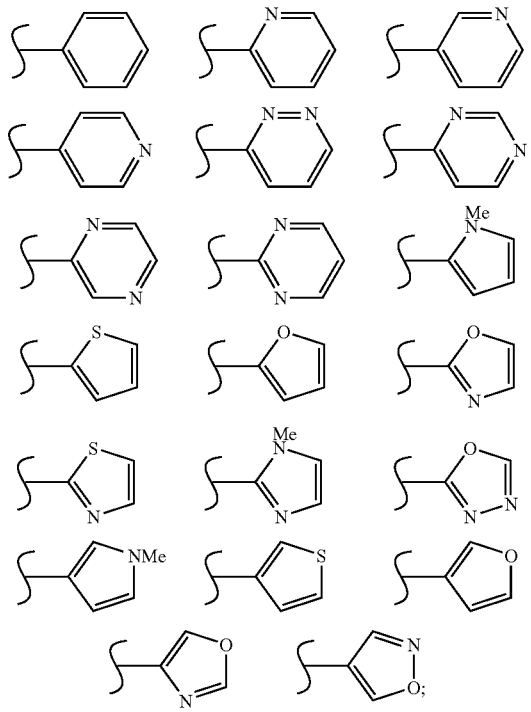

provided that $R^1$ and $R^2$ are not both hydrogen.

3. An inhibitor of fatty acid amide hydrolase according to claim 2 wherein the α-keto heterocyclic pharmacophore of the inhibition subunit A is:

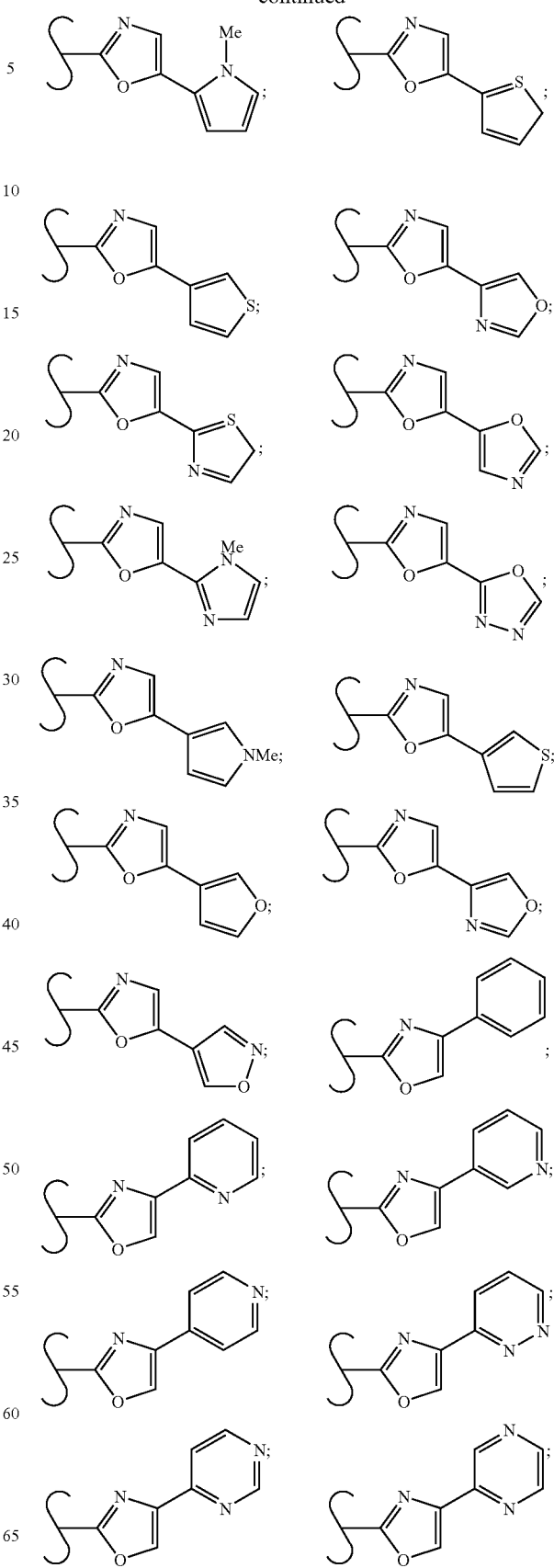

-continued

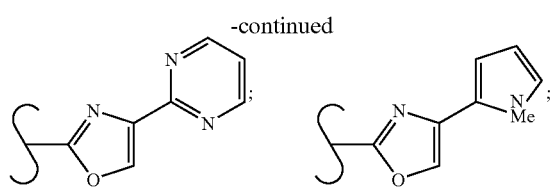
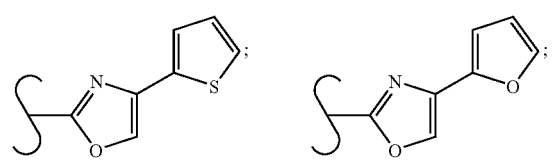
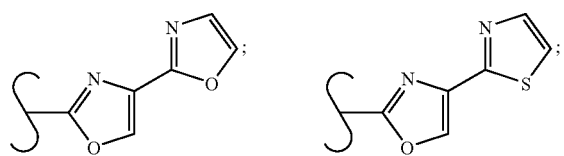
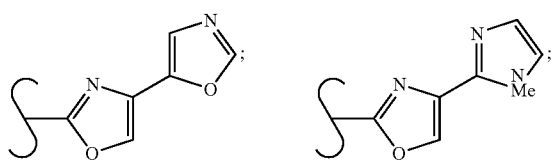
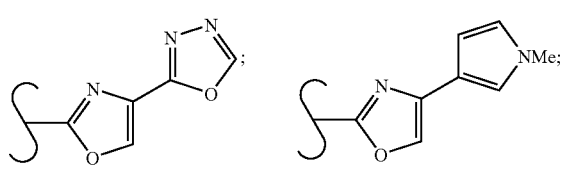
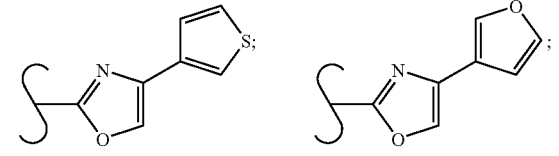
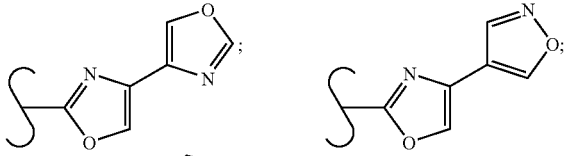
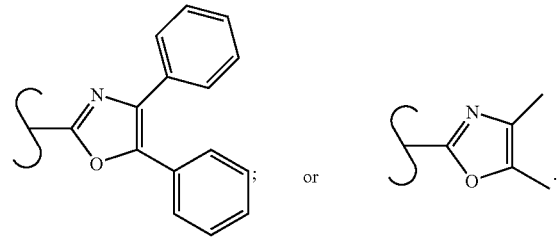

4. An inhibitor of fatty acid amide hydrolase according to claim 3 wherein the inhibitor is represented by the following structure:

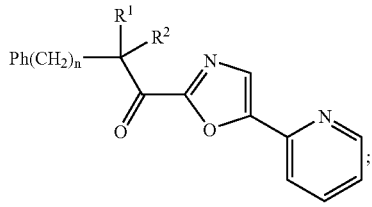

wherein $R^1$ and $R^2$ are independently selected from the group consisting of hydrogen, fluoro, chloro, hydroxyl, alkoxy, trifluoromethyl, and alkyl; and "n" is 2, 3, 4, 5, 6, 7, or 8.

5. An inhibitor of fatty acid amide hydrolase represented by the following formula:

A-B—C wherein A is an inhibition subunit in the form of an α-keto heterocyclic pharmacophore for inhibiting the fatty acid amide hydrolase, B is a linkage subunit, and C is a binding subunit wherein A-B—C is represented by the formula:

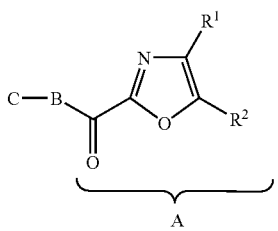

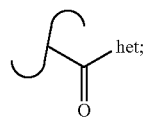

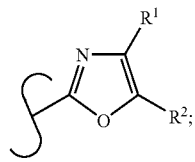

wherein $R^1$ is a radical selected from the group consisting of hydrogen, C1-C6 alkyl, aromatic ring, and heteroaromatic ring;

$R^2$ is a radical selected from the group consisting of hydrogen, C1-C6 alkyl, and heteroaromatic ring;

provided that $R^1$ and $R^2$ are not both hydrogen;

the linkage subunit B is a linear chain of 3 to 9 carbon atoms for linking the inhibition subunit A and the binding subunit C and for enabling the binding subunit C to bind to the binding region on the fatty acid amide hydrolase, the linear skeleton having a first end and a second end, the first end being covalently bonded to the α-keto group of A, wherein the first end of B is an α-carbon with respect to the α-keto group of the inhibition subunit A, and the α-carbon is optionally mono- or bis-functionalized with substituents selected from the group consisting of fluoro, chloro, hydroxyl, alkoxy, trifluoromethyl, and alkyl; and the binding subunit C is C1-C10 alkyl.

6. The inhibitor of fatty acid amide hydrolase according to claim 5 wherein $R^1$ and $R^2$ are radicals independently selected from the group consisting of hydrogen, C1-C6 alkyl, and radicals represented by the following structures:

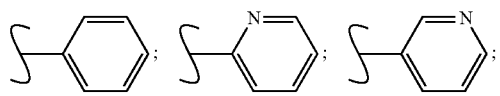

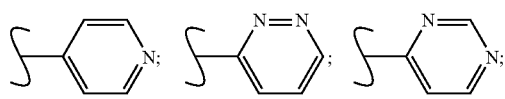

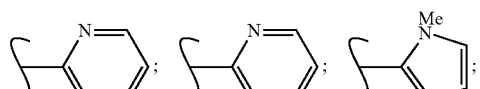

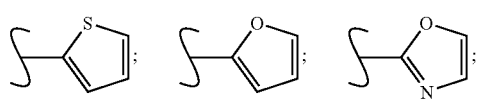

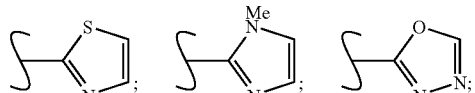

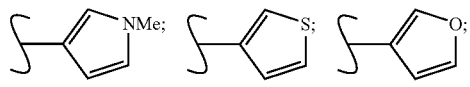

provided that $R^2$ is not phenyl.

7. The inhibitor of fatty acid amide hydrolase according to claim 6 wherein the α-keto heterocyclic pharmacophore of the inhibition subunit A is selected from:

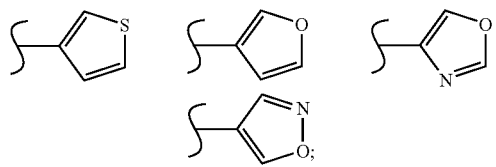

provided that $R^2$ is not phenyl.

8. The inhibitor of fatty acid amide hydrolase according to claim 7 wherein the inhibitor is represented by the following structure:

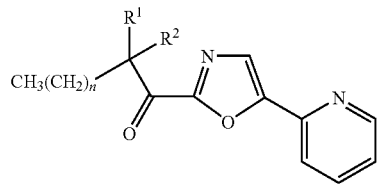

wherein $R^1$ and $R^2$ are independently hydrogen, fluoro, chloro, hydroxyl, alkoxy, trifluoromethyl, or alkyl; and "n" is 3, 4, 5, 6, 7, 8, or 9.

9. An inhibitor of fatty acid amide hydrolase represented by the formula:

A-B—C wherein A is an inhibition subunit in the form of an α-keto heterocyclic pharmacophore for inhibiting the fatty acid amide hydrolase, B is a linkage subunit, and C is a binding subunit wherein A-B—C is represented by the formula:

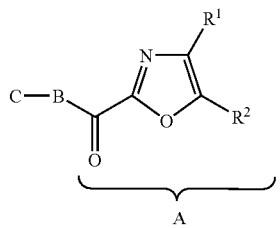

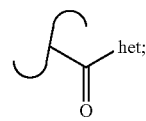

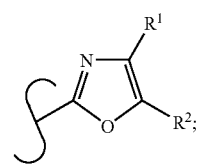

wherein
R$^1$ is a radical selected from the group consisting of hydrogen, C1-C6 alkyl, aromatic ring, and heteroaromatic ring;
R$^2$ is a radical selected from the group consisting of hydrogen, C1-C6 alkyl, and heteroaromatic ring;
provided that R$^1$ and R$^2$ are not both hydrogen;
the linkage subunit B is a linear chain of 3 to 9 carbon atoms for linking the inhibition subunit A and the binding subunit C and for enabling the binding subunit C to bind to the binding region on the fatty acid amide hydrolase, the linear skeleton having a first end and a second end, the first end being covalently bonded to the α-keto group of A, wherein the first end of B is an α-carbon with respect to the α-keto group of the inhibition subunit A, and the α-carbon is optionally mono- or bis-functionalized with substituents selected from the group consisting of fluoro, chloro, hydroxyl, alkoxy, trifluoromethyl, and alkyl; and the binding subunit C is a π-bond containing radical having a π-unsaturation and being an alkenyl having at least one unsaturation, with or without one or more heteroatoms, the binding subunit C being covalently bonded to the second end of the linkage subunit B, the π-unsaturation within the π-bond containing radical being separated from the α-keto group of A by a sequence of no less than 3 and no more than 9 atoms bonded sequentially to one another, inclusive of the linear skeleton for enabling the π-unsaturation to bind to the binding region of the fatty acid amide hydrolase while the inhibition subunit A inhibits the fatty acid amide hydrolase.

10. An inhibitor of fatty acid amide hydrolase according to claim 9 wherein $R^1$ and $R^2$ are radicals independently selected from the group consisting of hydrogen, C1-C6 alkyl, and radicals represented by the following structures:

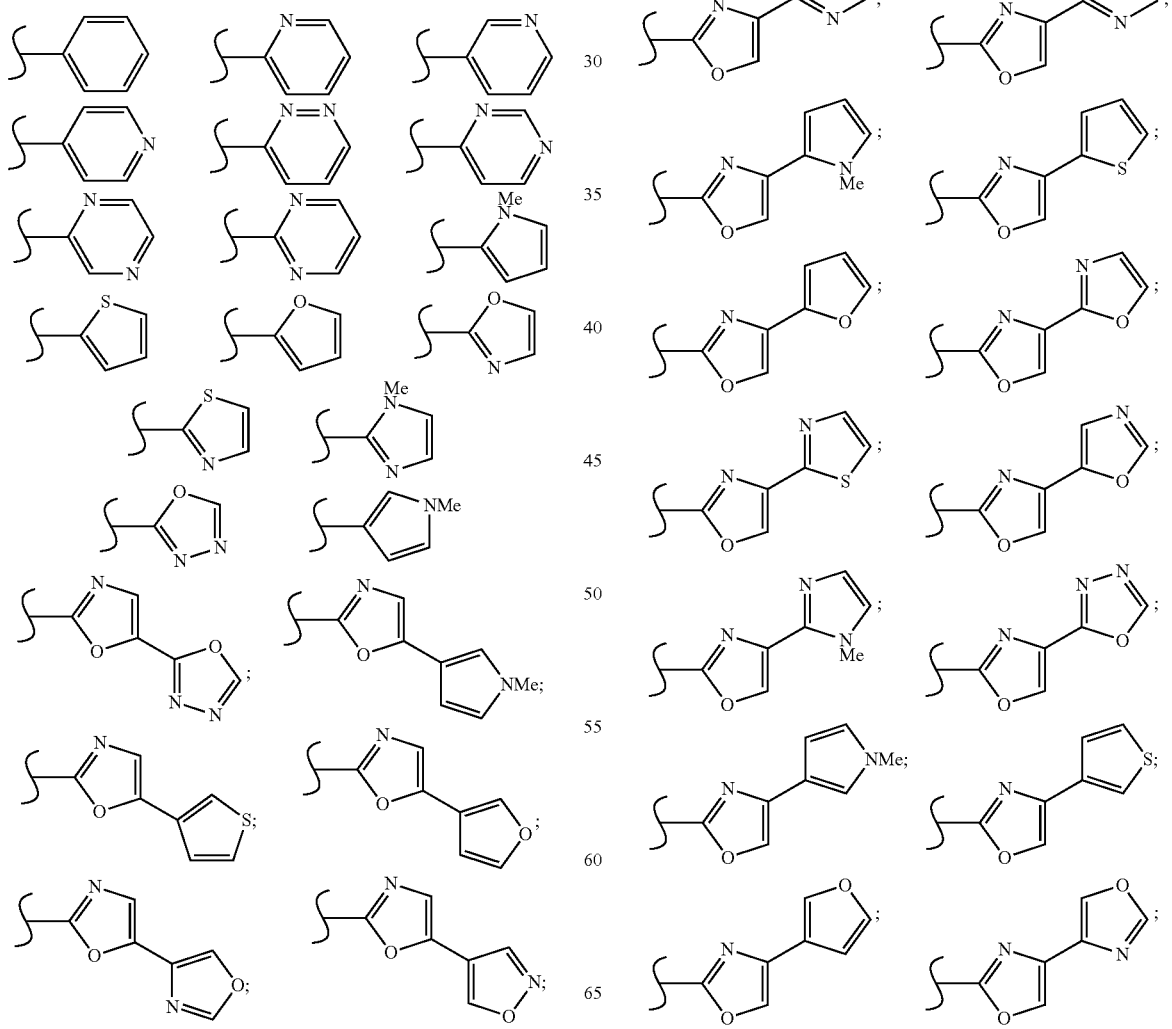

-continued
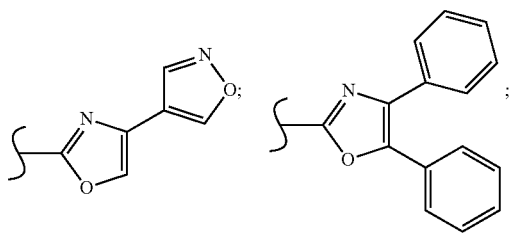; and
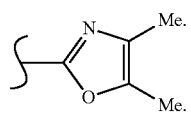
11. An inhibitor of fatty acid amide hydrolase according to claim 10 wherein the α-keto heterocyclic pharmacophore of the inhibition subunit A is selected from the following group:
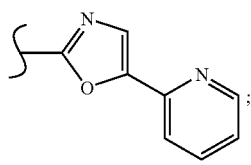; 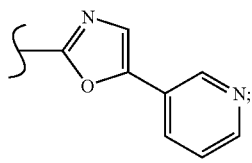;
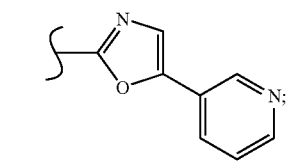
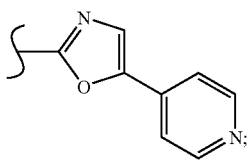; 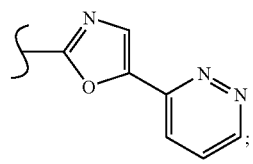;
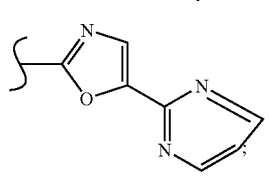; 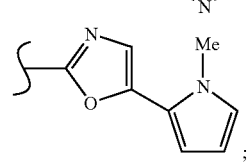;
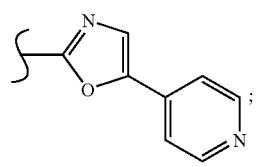; 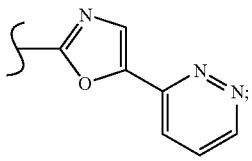;
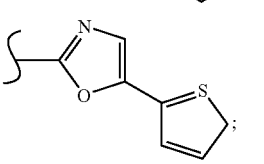; 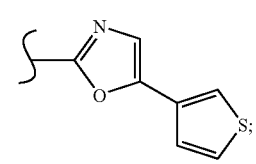;
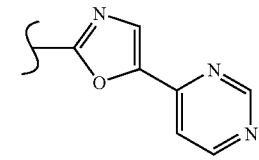; 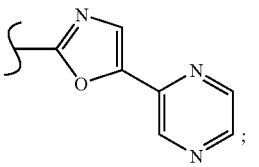;
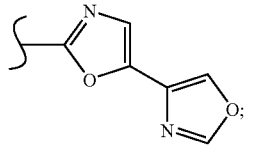; 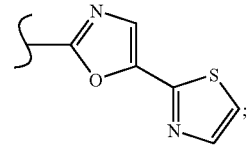;
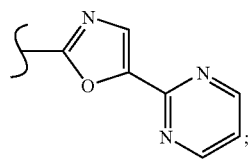; 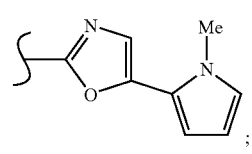;
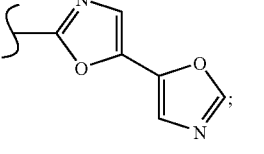; 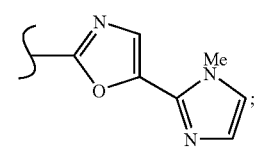;
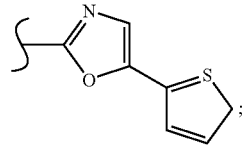; 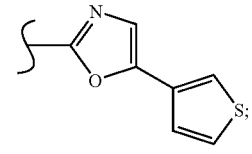;
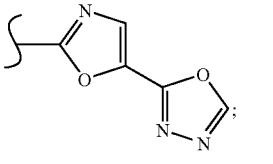; 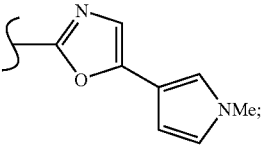;
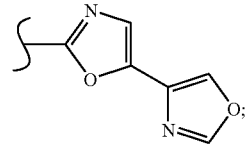; 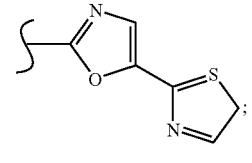;
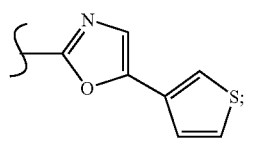; 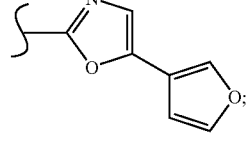;
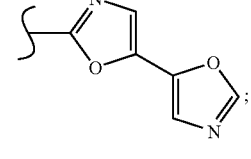; 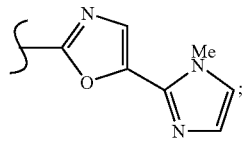;
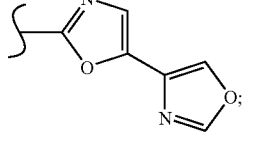; 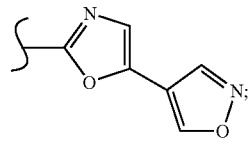;

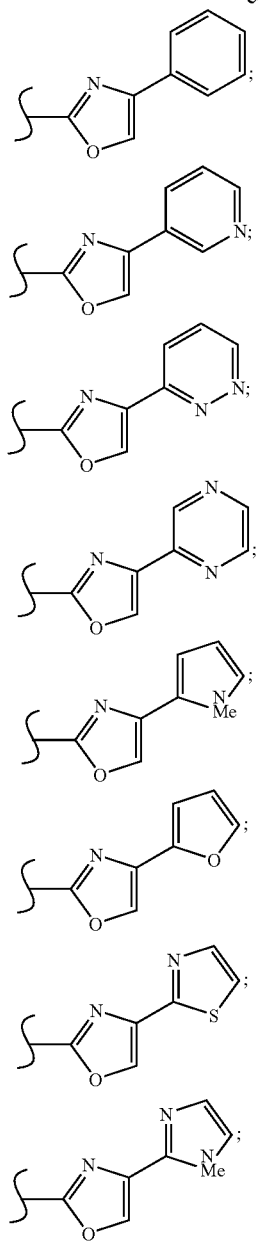
12. The inhibitor of fatty acid amide hydrolase according to claim 4 wherein one of $R^1$ and $R^2$ is hydrogen.
13. The inhibitor of fatty acid amide hydrolase according to claim 4 wherein "n" is 6, 7, or 8.
14. The inhibitor of fatty acid amide hydrolase according to claim 4 wherein the inhibitor is represented by the following structure:
* * * * *

UNITED STATES PATENT AND TRADEMARK OFFICE
CERTIFICATE OF CORRECTION

PATENT NO.        : 7,662,971 B2
APPLICATION NO.   : 10/528552
DATED             : February 16, 2010
INVENTOR(S)       : Dale L. Boger It is certified that error appears in the above-identified patent and that said Letters Patent is hereby corrected as shown below:

In column 1, line 32, delete "Cravaft," and insert -- Cravatt, --, therefor.

In column 9, line 2, delete "substituted," and insert -- substituted --, therefor.

In column 11, line 21, delete "oxo" and insert -- Oxo --, therefor.

In column 11, line 52, delete "$_1$H," and insert -- 1H, --, therefor.

In column 11, line 54, delete "yl]9(Z)" and insert -- yl]-9(Z) --, therefor.

In column 12, line 1, delete "powder" and insert -- powder: --, therefor.

In column 12, line 7, delete "(SiO$_{21}$" and insert -- (SiO$_2$, --, therefor.

In column 12, line 21, delete "1-[54(3" and insert -- 1-[5-(3 --, therefor.

In column 12, line 42, delete "9(Z)octadecene." and insert -- 9(Z)-octadecene. --, therefor.

In column 13, line 3, delete "(C$_{27}$H39NO$_2$" and insert -- (C$_{27}$H$_{39}$NO$_2$ --, therefor.

In column 13, line 5, delete "1-(4(" and insert -- 1-(4-( --, therefor.

In column 13, line 34, delete "1-(4(" and insert -- 1-(4-( --, therefor.

In column 13, line 40, delete "0C." and insert -- 0° C. --, therefor.

In column 13, line 63, delete "1-(4-Pyridin" and insert -- 1-(4-(Pyridin --, therefor.

In column 14, line 23, delete "r/z" and insert -- m/z --, therefor.

In column 15, line 43, delete "cm$^{31\ 1}$;" and insert -- cm$^{-1}$; --, therefor.

Signed and Sealed this

Third Day of August, 2010

David J. Kappos
*Director of the United States Patent and Trademark Office*

CERTIFICATE OF CORRECTION (continued)
U.S. Pat. No. 7,662,971 B2

In column 16, line 28, delete "m/z300.1911" and insert -- m/z 300.1911 --, therefor.

In column 17, line 46, delete "powder" and insert -- powder: --, therefor.

In column 17, line 49, delete "0.68" and insert -- 0.86 --, therefor.

In column 17, line 49, delete "13C" and insert -- $^{13}$C --, therefor.

In column 18, line 13, delete "13C" and insert -- $^{13}$C --, therefor.

In column 18, line 19, delete "1 (5" and insert -- 1-(5 --, therefor.

In column 18, line 41, delete "powder" and insert -- powder: --, therefor.

In column 18, line 46, delete "u." and insert -- u$_{max}$ --, therefor.

In column 18, line 48, delete "m/z253.0950" and insert -- m/z 253.0950 --, therefor.

In column 19, line 13, delete "$^{0°}$ C." and insert -- 0° C. --, therefor.

In column 19, line 28, delete "u." and insert -- u$_{max}$ --, therefor.

In column 19, line 39, delete "yl]4" and insert -- yl]-3 --, therefor.

In column 19, line 46, delete "yl].4" and insert -- yl]-4 --, therefor.

In column 19, line 57, delete "5phenylpentanoic" and insert -- 5-phenylpentanoic --, therefor.

In column 20, line 19, delete "powder" and insert -- powder: --, therefor.

In column 20, line 20, delete "ml/z" and insert -- m/z --, therefor.

In column 20, line 35, delete "(SiO$_{21}$," and insert -- (SiO$_2$, --, therefor.

In column 20, line 45, delete "powder" and insert -- powder: --, therefor.

In column 20, line 50, delete "cm,20%" and insert -- cm, 20% --, therefor.

In column 20, line 52, delete "powder" and insert -- powder: --, therefor.

In column 21, lines 12-20, delete "4,5 . . . 3H)." and insert the same after "(213)" on Col. 21, Line 11, as a continuation of same paragraph.

In column 21, line 22, delete "yl)- -oxo" and insert -- yl)-1-oxo --, therefor.

CERTIFICATE OF CORRECTION (continued)
U.S. Pat. No. 7,662,971 B2

In column 22, lines 20-30, in Claim 1, delete " 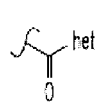 " and insert -- ; --, therefor.

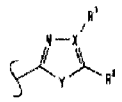

In column 24, line 20, in Claim 3, delete " 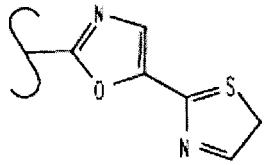 " and insert

-- 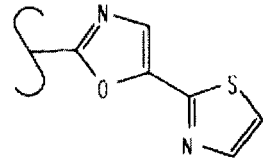 --, therefor.

In column 25, lines 60-65, in Claim 3, delete " 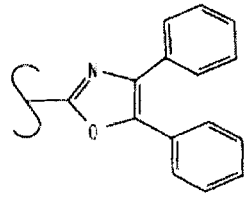 " and insert

-- 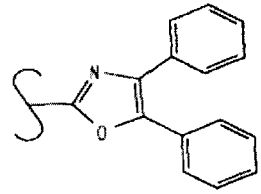 --, therefor.

In column 26, lines 40-55, in Claim 5, delete " 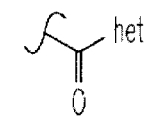 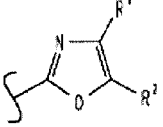 " and insert -- ; --, therefor.

CERTIFICATE OF CORRECTION (continued)
U.S. Pat. No. 7,662,971 B2

In column 27, lines 57-67, in Claim 7, below "from:" delete

" 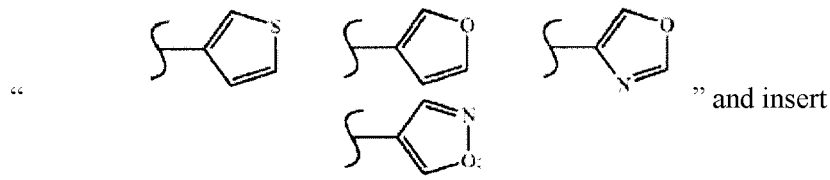 " and insert

-- 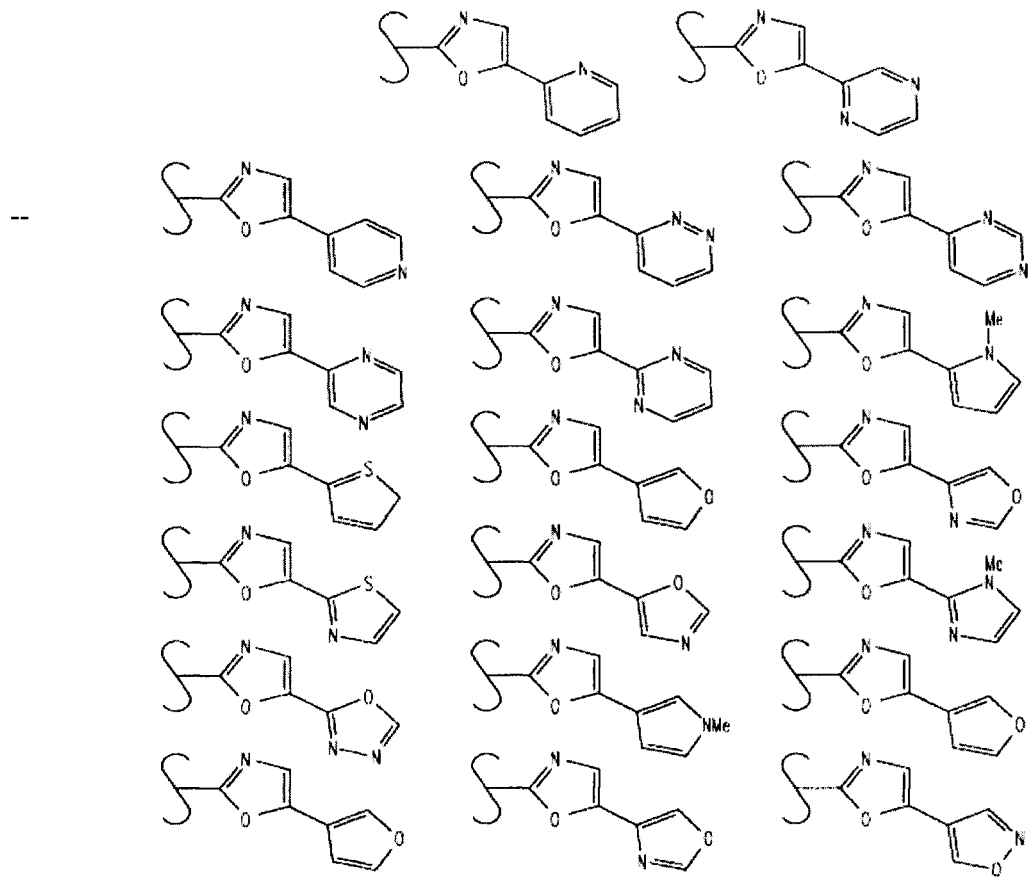

provided that $R^2$ is not phenyl. --

CERTIFICATE OF CORRECTION (continued)
U.S. Pat. No. 7,662,971 B2

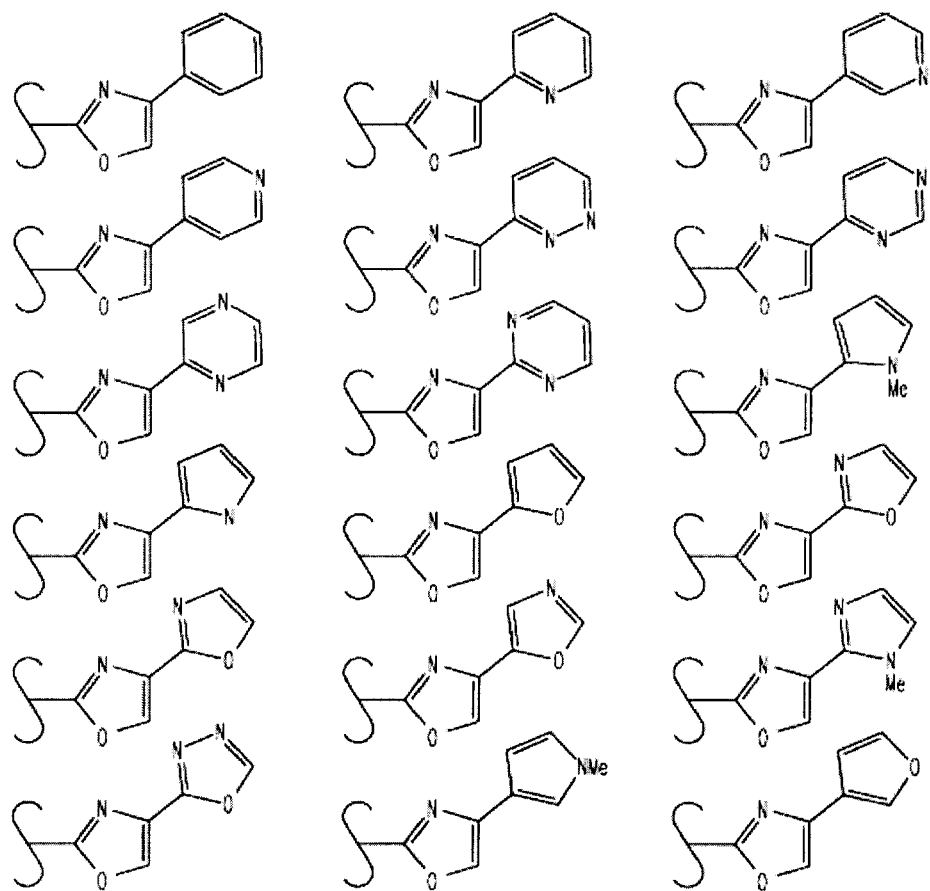

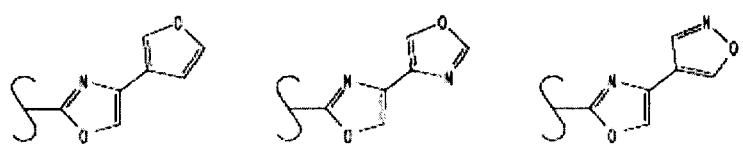

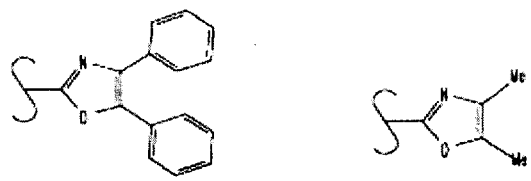

--, therefor.

CERTIFICATE OF CORRECTION (continued)
U.S. Pat. No. 7,662,971 B2

In column 28, lines 40-55, in Claim 9, delete " 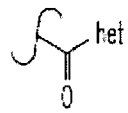 " and insert -- ; --.

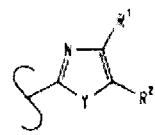

In columns 29-30, lines 50-65, and column 31, lines 1-15, in Claim 10, below " 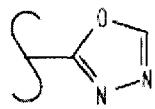 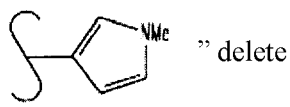 " delete

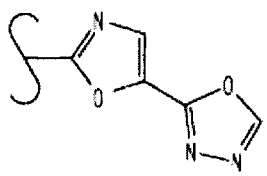   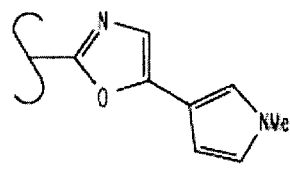

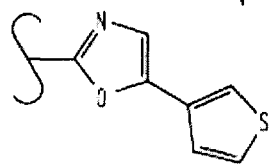   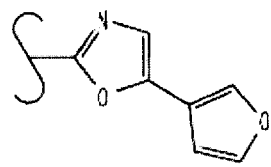

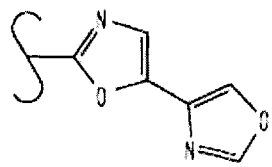   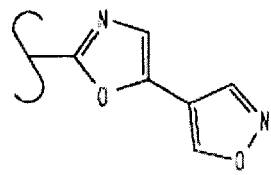

"

CERTIFICATE OF CORRECTION (continued)
U.S. Pat. No. 7,662,971 B2

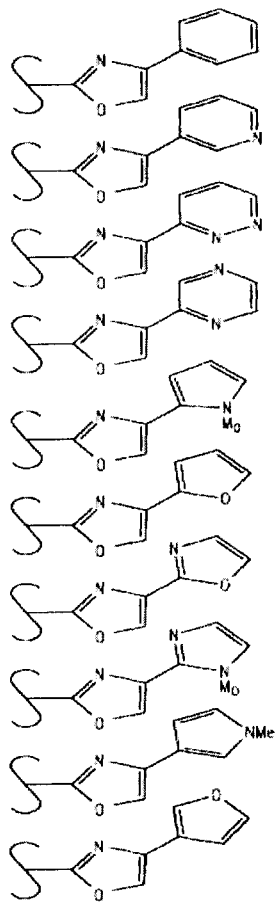 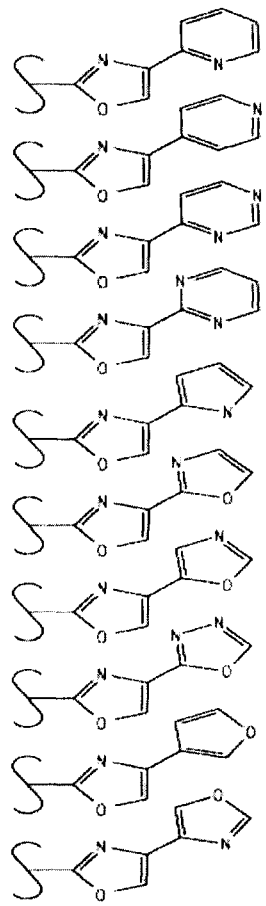

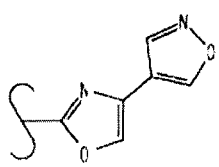 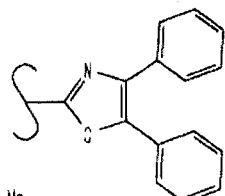  " and insert

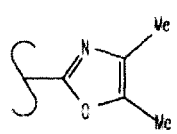

-- 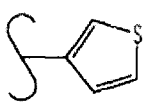 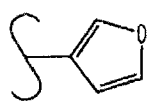 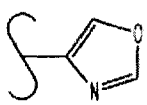 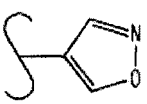 --, therefor.

CERTIFICATE OF CORRECTION (continued)
U.S. Pat. No. 7,662,971 B2

In column 31, lines 55-60, in Claim 11, delete " 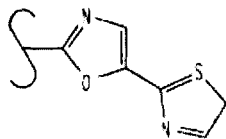 " and insert

-- 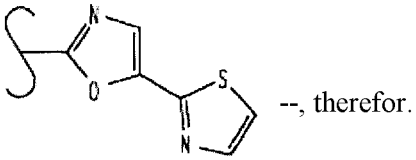 --, therefor.

In column 32, lines 1-45, in Claim 11, below " 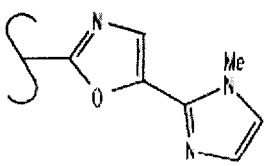 " delete

"
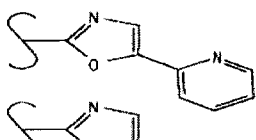 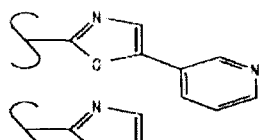
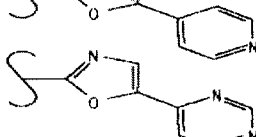 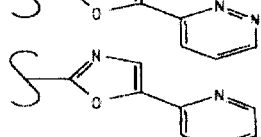
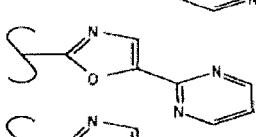 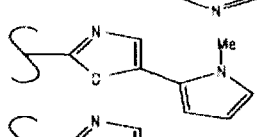
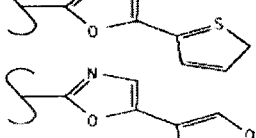 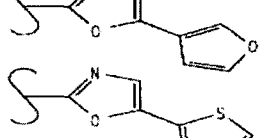
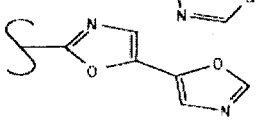 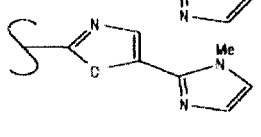
 
".

CERTIFICATE OF CORRECTION (continued)
U.S. Pat. No. 7,662,971 B2

In column 34, line 20, in Claim 11, delete " 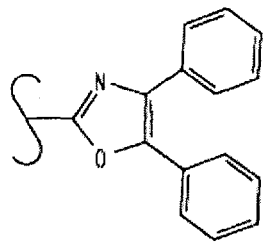 " and insert

-- 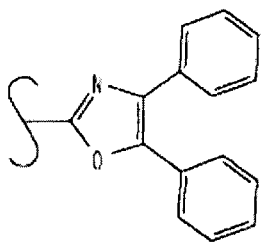 --, therefor.

UNITED STATES PATENT AND TRADEMARK OFFICE
CERTIFICATE OF CORRECTION

PATENT NO. : 7,662,971 B2  Page 1 of 1
APPLICATION NO. : 10/528552
DATED : February 16, 2010
INVENTOR(S) : Dale L. Boger It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1080 days.

Signed and Sealed this

Twenty-eighth Day of December, 2010

David J. Kappos
*Director of the United States Patent and Trademark Office*